(12) United States Patent
BenDavid

(10) Patent No.: US 12,409,021 B2
(45) Date of Patent: Sep. 9, 2025

(54) INFERIOR-TO-SUPERIOR DEEP TISSUE THREAD-LIFT USING POLYDIOXANONE THREADS

(71) Applicant: Dina BenDavid, Edgartown, MA (US)

(72) Inventor: Dina BenDavid, Edgartown, MA (US)

(*) Notice: Subject to any disclaimer, the term of this patent is extended or adjusted under 35 U.S.C. 154(b) by 263 days.

(21) Appl. No.: 18/365,360

(22) Filed: Aug. 4, 2023

(65) Prior Publication Data

US 2024/0041583 A1    Feb. 8, 2024

Related U.S. Application Data

(60) Provisional application No. 63/370,449, filed on Aug. 4, 2022.

(51) Int. Cl.
*A61F 2/00* (2006.01)
*A61B 17/06* (2006.01)
*A61B 17/34* (2006.01)

(52) U.S. Cl.
CPC ........ *A61F 2/0059* (2013.01); *A61B 17/3468* (2013.01); *A61B 2017/06176* (2013.01); *A61F 2220/0016* (2013.01)

(58) Field of Classification Search
None
See application file for complete search history.

(56) References Cited

U.S. PATENT DOCUMENTS

| | | | |
|---|---|---|---|
| 9,480,473 B2* | 11/2016 | Kim | A61B 17/0401 |
| 10,178,990 B2* | 1/2019 | Kim | A61B 17/0469 |
| 10,226,320 B2* | 3/2019 | Kim | A61F 2/0059 |
| 11,911,255 B1* | 2/2024 | Busso | A61B 17/3468 |
| 2005/0267531 A1* | 12/2005 | Ruff | A61B 17/064 606/228 |
| 2007/0173887 A1* | 7/2007 | Sasaki | A61F 2/0059 606/232 |
| 2008/0009902 A1* | 1/2008 | Hunter | A61K 9/0024 606/228 |
| 2008/0132931 A1* | 6/2008 | Mueller | A61B 17/0482 206/570 |
| 2008/0132945 A1* | 6/2008 | Mueller | A61B 17/0483 606/232 |
| 2009/0226500 A1* | 9/2009 | Avelar | A61L 31/16 514/183 |
| 2011/0160578 A1* | 6/2011 | Tripathi | A61B 90/37 600/427 |
| 2013/0041397 A1* | 2/2013 | Nishimura | A61H 39/086 606/189 |
| 2017/0049972 A1* | 2/2017 | Persons | A61M 19/00 |
| 2017/0259013 A1* | 9/2017 | Boyden | G16H 30/40 |
| 2021/0068826 A1* | 3/2021 | Moore | A61B 17/06166 |
| 2021/0346018 A1* | 11/2021 | Moore | D01G 3/00 |

(Continued)

*Primary Examiner* — Shaun L David
(74) *Attorney, Agent, or Firm* — Intrinsic Law Corp.

(57) ABSTRACT

A thread-lifting surgical procedure employs an inferior-to-superior method of thread insertion through one or more deep cheek tissue pads, which angles the deep cheek tissue fat pads upward and inward. An inferior-to-superior method of thread insertion is also used for gonial angle insertion vectors through the superficial fat pads. A method for marking the patient prior to performing the thread-lifting surgical procedure is also provided. A computer and computerized method are disclosed for automated planning, execution and display of the present invention.

16 Claims, 29 Drawing Sheets

(56) References Cited

U.S. PATENT DOCUMENTS

| | | | | |
|---|---|---|---|---|
| 2021/0353822 A1* | 11/2021 | Cho | ............... | A61L 17/005 |
| 2023/0020956 A1* | 1/2023 | Wall | ............... | A61L 17/10 |
| 2023/0355233 A1* | 11/2023 | Yu | ............... | A61B 17/06166 |
| 2024/0218572 A1* | 7/2024 | Song | ............... | A61B 17/06 |
| 2024/0293116 A1* | 9/2024 | Song | ............... | A61B 17/06166 |

* cited by examiner

INFERIOR-TO-SUPERIOR DEEP TISSUE THREAD-LIFT USING POLYDIOXANONE THREADS

CROSS-REFERENCE TO RELATED APPLICATIONS

This application claims priority to U.S. Provisional Application No. 63/370,449, titled "Inferior-to-Superior Deep Tissue Thread-Lift Using PDO Threads," filed on Aug. 4, 2022, which is hereby incorporated by reference.

TECHNICAL FIELD

This application relates generally to cosmetic medical procedures and equipment.

BACKGROUND

Loss of tissue elasticity and volume are part of aging. Signs of aging result from chronological changes in underlying soft tissue structures. In the face, such changes can appear as jowl formation and deepening nasolabial folds. Another factor affecting facial appearance during aging is gravity, which causes ptosis of the facial soft tissue, such as a downward shift of the malar fat pad that creates hollowness of the mid-facial and infra-orbital areas.

Surgical lifting with general anesthesia is a highly invasive procedure involving potential perioperative complications in addition to prolonged procedural downtime and scarring. Although surgical facelifts have long been considered the gold standard for facial rejuvenation, the development of and interest in minimally invasive techniques have grown dramatically in recent years.

Thread lifting has been used as an alternative to traditional plastic surgeries. Thread lifting is a cosmetic procedure that lifts and realigns sagging tissue, while adding definition to facial contours by using threads that are manufactured from the same materials used in surgery to close wounds. When placed under the skin, the threads can be used to tighten the tissue and add volume to the area of application.

In conventional thread lifting procedures, the threads are inserted (e.g., as vectors) in a superior-to-inferior direction 10, as illustrated in FIG. 1. In addition, the threads are conventionally inserted in the superficial fat pads. An example illustration of the superficial fat pads 20 is provided in FIG. 2.

Thread lifting was first promoted in the 1990s when the first barbed suture made of nonabsorbable polypropylene was developed. However, the nonabsorbable nature of this thread made it prone to a number of complications. Absorbable polydioxanone (PDO) barbed threads were introduced a decade later, which proved a safer and effective alternative to nonabsorbable threads.

PDO is a synthetic and absorbable colorless polymer and is used for sutures that are metabolized in the body after fulfilling their purpose. PDO has been in use for over three decades in tissue engineering and surgery. It is considered safe and is used on a daily basis in hospitals for wound closure. There are no remarkable problems with allergic reactions or long-term complications. FIG. 3 illustrates the chemical structure of PDO and the p-dioxanone monomer from which it is synthesized. PDO is degraded by hydrolysis and is completely metabolized in the body. Due to its relatively prolonged absorption duration (182-238 days), PDO is widely used where a long-lasting absorbable material is desirable.

Barbed (or cogged) threads are mainly used in thread lifting procedures. A cog, which looks like a thorn, is produced by a cutting or molding method in accordance with the direction of pulling. Barbs along the thread act as cogs to grasp, lift, and support the facial tissue. The barbs open like an umbrella when pulled to form a support structure that lifts sagging tissue. This creates tension in the thread, and the tension lifts the skin tissue.

There are three types of barbed thread patterns: unidirectional, bi-directional and multi-directional. The barbed pattern design used is dependent on the method of insertion and lifting effect desired.

Ideal candidates for thread lifts include patients with minimal to moderate signs of aging, deeper nasolabial folds, and ptosis of the malar fat pad. Thread lifting is best suited for patients aged between 25 and 50 years, with mild to moderate facial ptosis and adequate facial volume, and who desire a procedure without scars and who do not want to undergo a surgical procedure.

Thread lifting procedures share in common the placement of barbed sutures underneath sagging tissue along a specific trajectory to address ptosis. The traditional procedure involves cogged threads which are inserted in the subcutaneous fat layer with a needle/cannula, which is then removed, resulting in the thread remaining intact in the tissue while gently being pulled to achieve the desired skin lift. The thread is then trimmed at the entry point without knotting. Example cross-sectional views of a traditional thread lifting procedure are illustrated in FIGS. 4A-D.

Throughout the literature, various terminology was used to describe the depth of traditional thread lifting; however, the consensus was to use the terminology of subcutaneous or SMAS (superficial musculoaponeurotic system) layer, which was also referred to as "subdermal" in general terms (see FIG. 5). While there were some variations in the literature with regards to thread types used and method of insertion in traditional procedures, there was one constant in all the literature: the insertion depth of PDO threads is always in the subcutaneous fat or SMAS.

SUMMARY

Example embodiments described herein have innovative features, no single one of which is indispensable or solely responsible for their desirable attributes. The following description and drawings set forth certain illustrative implementations of the disclosure in detail, which are indicative of several example ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a method comprising (a) forming pilot holes at respective insertion points on a first anatomical side of a patient, the respective insertion points comprising: a first cheek insertion point located about 1.5 cm along a submalar contour line of the patient from a nasolabial fold line of the patient; a plurality of additional cheek insertion points spaced about 1 cm from each other along the submalar contour line, the additional cheek insertion points including a second cheek insertion point located about 1 cm along the submalar contour line from the first cheek insertion point; and a gonial angle insertion point located about 2 cm superior to a gonial angle of the patient. The method further comprises (b) inserting a first cannula into a first pilot hole at the first cheek insertion point, the first cannula having an L-shaped distal end, the first cannula containing a first multidirectional barbed polydioxanone (PDO) thread, the first cannula oriented at an angle of about 90 degrees with respect to a skin surface of the patient; (c) advancing the first cannula about 3 mm to about 5 mm into the first pilot hole while maintaining the angle of the first cannula at about 90 degrees with respect to the skin surface of the patient; (d) reducing the angle of the first cannula to about 10 degrees with respect to the skin surface of the patient; (e) advancing the first cannula about 1 cm while maintaining the angle of the first cannula at about 10 degrees with respect to the skin surface of the patient so as to advance the first cannula into one or more deep cheek fat pads; (f) reducing the angle of the first cannula to about 0 degrees with respect to the skin surface of the patient; (g) advancing, while maintaining the angle of the first cannula at about 0 degrees with respect to the skin surface of the patient, the first cannula along a cheek insertion vector to an end point that represents a levator labii superioris alaeque nasi of the patient, whereby the cheek insertion vector extends in an inferior-to-superior direction through the one or more deep cheek fat pads; (h) removing the first cannula from the first cheek insertion point; (i) cutting an exposed portion of the first multidirectional barbed PDO thread; (j) repeating steps (b) through (h) for each of the additional cheek insertion points using a respective multidirectional barbed PDO thread; (k) inserting a second cannula into a gonial angle pilot hole at the gonial angle insertion point, the second cannula containing a second PDO thread, the second cannula oriented at an angle of about 90 degrees with respect to the skin surface of the patient; (l) advancing the second cannula about 2 mm to about 3 mm into the gonial angle pilot hole while maintaining the angle of the second cannula at about 90 degrees with respect to the skin surface of the patient; (m) reducing the angle of the second cannula to about 0 degrees with respect to the skin surface of the patient; (n) advancing the second cannula along a first gonial angle vector while maintaining the angle of the second cannula at about 0 degrees with respect to the skin surface of the patient, the first gonial angle vector beginning at the gonial angle insertion point and ending at a hairline of the patient along a first line, the first line passing about 1 cm from a tragus of the patient, whereby the first gonial angle vector extends in an inferior-to-superior insertion direction; (o) removing the second cannula from the gonial angle insertion point; (p) cutting an exposed portion of the second PDO thread; (q) inserting the second cannula into the gonial angle pilot hole at the gonial angle insertion point, the second cannula containing a third PDO thread, the second cannula oriented at the angle of about 90 degrees with respect to the skin surface of the patient; (r) advancing the second cannula about 2 mm to about 3 mm into the gonial angle pilot hole while maintaining the angle of the second cannula at about 90 degrees with respect to the skin surface of the patient; (s) reducing the angle of the second cannula to about 0 degrees with respect to the skin surface of the patient; (t) advancing the second cannula along a second gonial angle vector while maintaining the angle of the second cannula at about 0 degrees with respect to the skin surface of the patient, the second gonial angle vector beginning at the gonial angle insertion point and ending at a hairline of the patient along a second line that is medial to the first line, the second line passing about 3 cm lateral to a lateral canthus of the patient along a horizontal line that passes through the lateral canthus, the second gonial angle vector extends in the inferior-to-superior insertion direction; (u) removing the second cannula from the gonial angle insertion point; and (v) cutting an exposed portion of the third PDO thread.

In one or more embodiments, the first cannula is different than the second cannula. In one or more embodiments, after removing the first cannula from the first cheek insertion point, a dimple in the patient is located at the first cheek insertion point and the method further comprises (w) pushing the dimple of the patient inwardly along the first multidirectional barbed PDO thread. In one or more embodiments, the method further comprises (x) pressing a finger along the cheek insertion vector to suspend upwards one or more deep fat pads in the patient. In one or more embodiments, step (j) comprises repeating steps (b) through (h), (w), and (x) for each of the additional cheek insertion points, the first cannula being advanced along a respective cheek insertion vector at each additional cheek insertion point.

In one or more embodiments, the method further comprises rotating the first cannula while removing the first cannula from the first cheek insertion point. In one or more embodiments, the method further comprises rotating the second cannula while removing the second cannula from the gonial angle insertion point in steps (o) and (u).

In one or more embodiments, the method further comprises repeating steps (a) through (v) on a second anatomical side of the patient. In one or more embodiments, the first anatomic side of the patient is an anatomical left side of the patient and the second anatomic side of the patient is an anatomical right side of the patient.

In one or more embodiments, the second PDO thread comprises a second multidirectional barbed PDO thread or a second bi-directional barbed PDO thread, and the third PDO thread comprises a third multidirectional barbed PDO thread or a third bi-directional barbed PDO thread.

Another aspect of the invention is directed to a method of marking a face of a patient for a surgical procedure, the method comprising: on a first anatomical side of the patient: (a) marking on the patient, with a surgical marking pen, a first line on a nasolabial fold line of the patient; (b) drawing on the patient, with the surgical marking pen, a horizontal line starting at a lateral canthus of the patient, the horizontal extending at least 2 cm in length; (c) drawing on the patient, with the surgical marking pen, a vertical line from the horizontal line to a mandible of the patient, the vertical line intersecting the horizontal line at a point about 2 cm from a respective lateral canthus of the patient, the vertical line orthogonal to the horizontal line; (d) drawing on the patient, with the surgical marking pen, a submalar contour line from an oral commissure of the patient to a lower tragus of the patient; (e) marking on the patient, with the surgical marking pen, a first cheek insertion point on the submalar contour line, the first cheek insertion point located about 1.5 cm lateral to the first line; (f) marking on the patient, with the surgical marking pen, additional cheek insertion points on the submalar contour line, the additional cheek insertion points spaced about 1 cm from each other along the submalar contour line, the additional cheek insertion points including a second cheek insertion point located about 1 cm along the submalar contour line from the first cheek insertion point; (g) marking on the patient, with the surgical marking pen, a levator labii superioris alaeque nasi of the patient; (h) marking on the patient, with the surgical marking pen, a gonial angle of the patient; (i) marking on the patient, with the surgical marking pen, a gonial angle insertion point on the patient, the gonial angle insertion point located about 2 cm above the gonial angle and anterior to an earlobe of the patient; (j) drawing on the patient, with the surgical marking pen, a first line on the patient, the first line extending from the gonial angle insertion point to a hairline of the patient, the first line passing about 1 cm from a tragus of the patient, the first line representing a first gonial angle vector that extends in an inferior-to-superior insertion direction from the gonial angle insertion point to the hairline; and (k) drawing, with the surgical marking pen, a second line on the patient, the second line extending from the gonial angle insertion point to the hairline, the second line medial to the first line and passing about 1 cm from the point of intersection of the horizontal and vertical lines, the second line representing a second gonial angle vector that extends in an inferior-to-superior insertion direction from the gonial angle insertion point to the hairline.

In one or more embodiments, the method further comprises drawing a plurality of cheek lines on the patient, the cheek lines including: a first cheek line that extends from the first cheek insertion point to a mark on the levator labii superioris alaeque nasi, a second cheek line that extends from the second cheek insertion point to the mark on the levator labii superioris alaeque nasi, and a plurality of additional cheek lines, each additional cheek line extends from a respective additional cheek insertion point to the mark on the levator labii superioris alaeque nasi, wherein the plurality of cheek lines represent respective cheek vectors that extend in the inferior-to-superior insertion direction.

In one or more embodiments, the method further comprises repeating steps (a) through (k) on a second anatomical side of the patient. In one or more embodiments, the first anatomic side of the patient is an anatomical left side of the patient and the second anatomic side of the patient is an anatomical right side of the patient.

In one or more embodiments, graphical instructions for performing a surgical procedure are displayed on a display screen in electrical communication with a computer, the graphical instructions including a graphical illustration of each step of the surgical method of claim 1.

BRIEF DESCRIPTION OF THE DRAWINGS

For a fuller understanding of the nature and advantages of the concepts disclosed herein, reference is made to the detailed description of preferred embodiments and the accompanying drawings.

DETAILED DESCRIPTION

Figure 1:
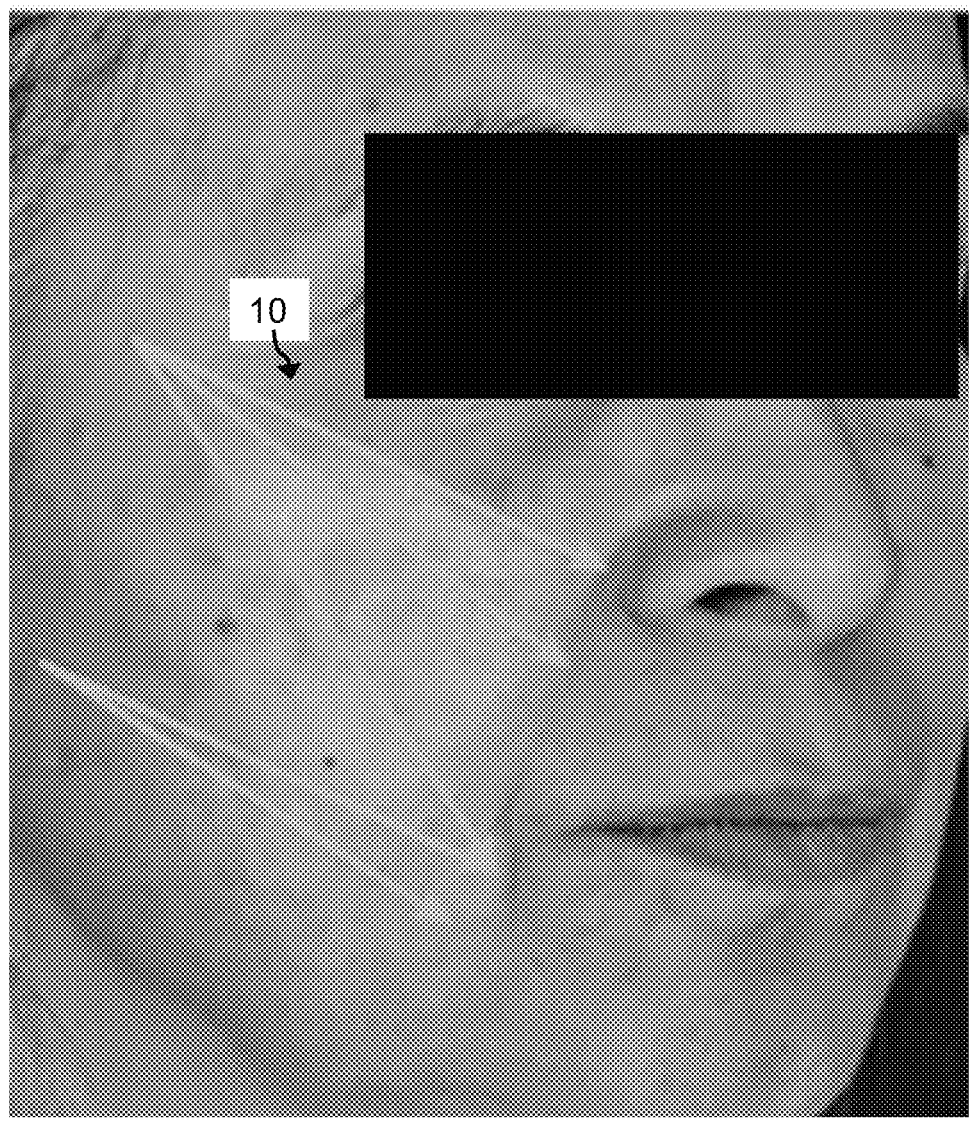
FIG. 1 illustrates thread insertion vectors in conventional thread lifting procedures.
Figure 2:
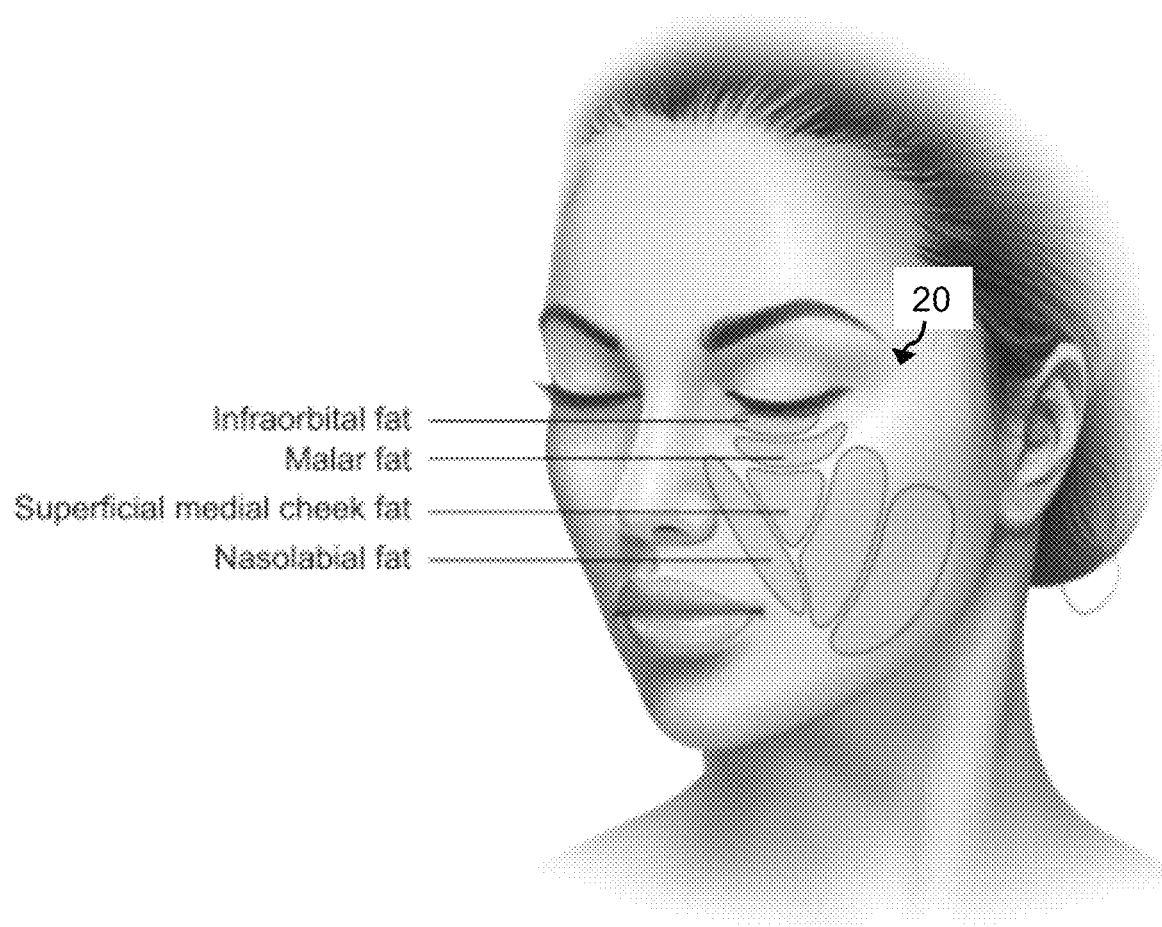
FIG. 2 is an example illustration of superficial fat pads according to the prior art.
Figure 3:
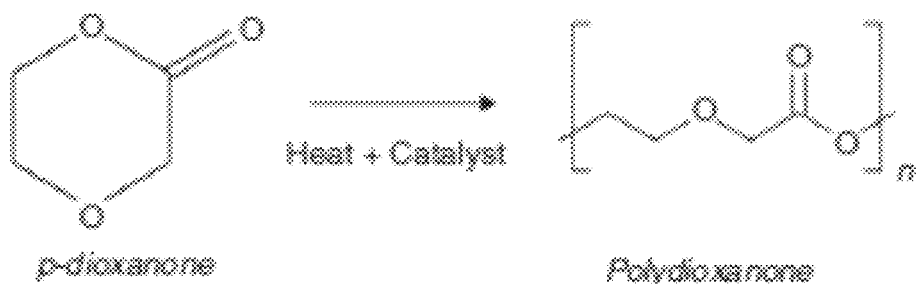
FIG. 3 illustrates the chemical structure of PDO and the p-dioxanone monomer from which it is synthesized.
Figure 4A:
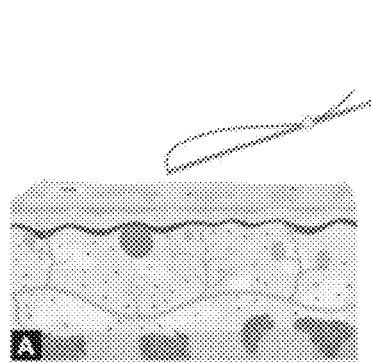
FIGS. 4A-D are cross-sectional views of a traditional thread lifting procedure according to the prior art.
Figure 4B:
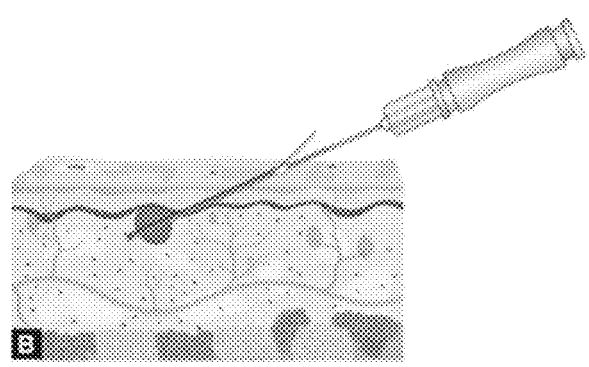
Figure 4C:
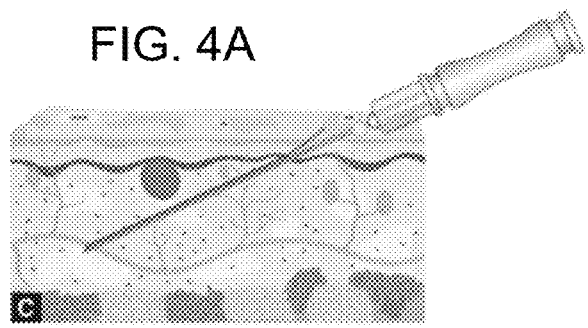
Figure 4D:
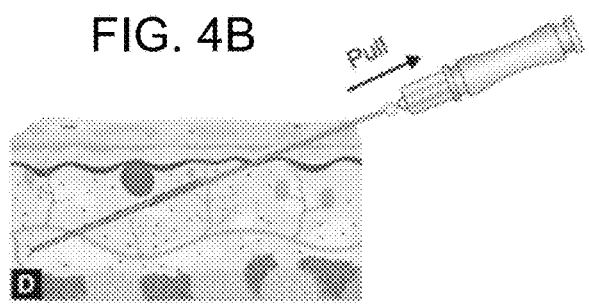
Figure 5:
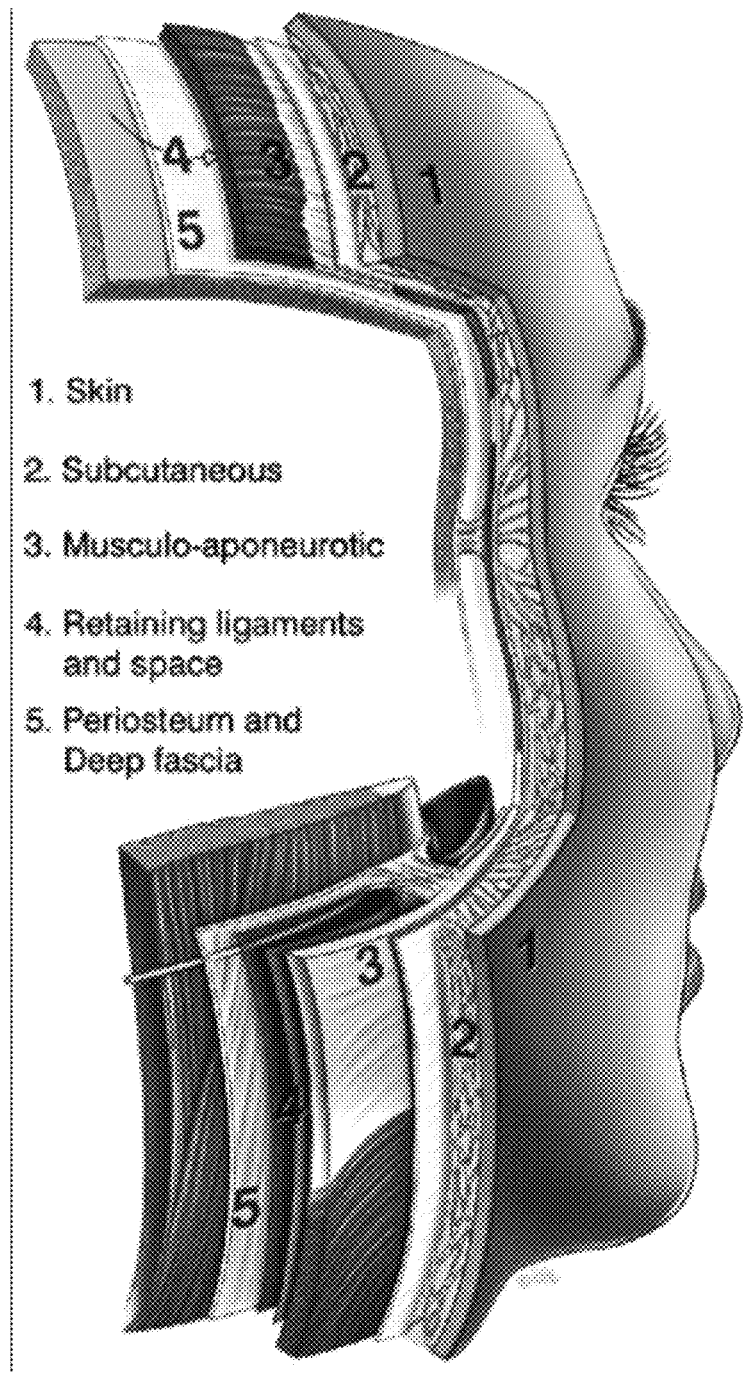
FIG. 5 is an exploded view of layers of a human face according to the prior art.
Figure 6:
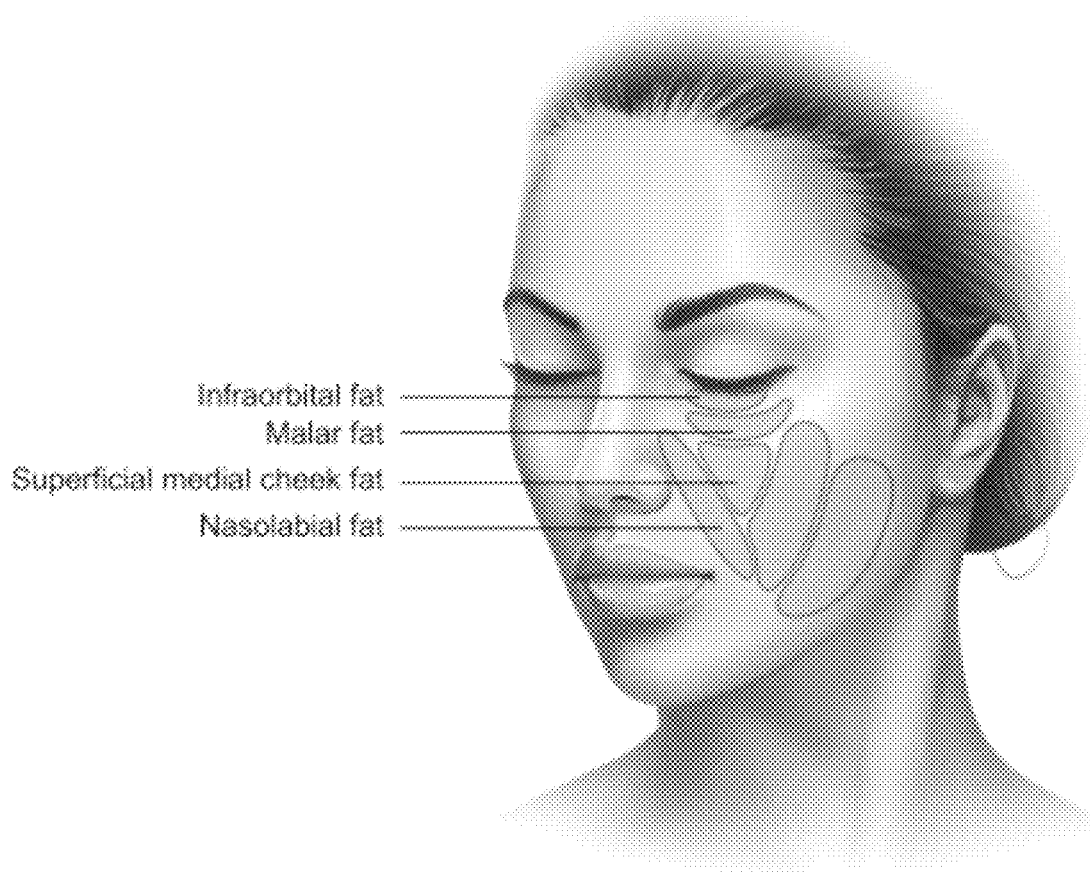
FIG. 6 illustrates superficial fat pads of a human face according to the prior art.
Figure 7:
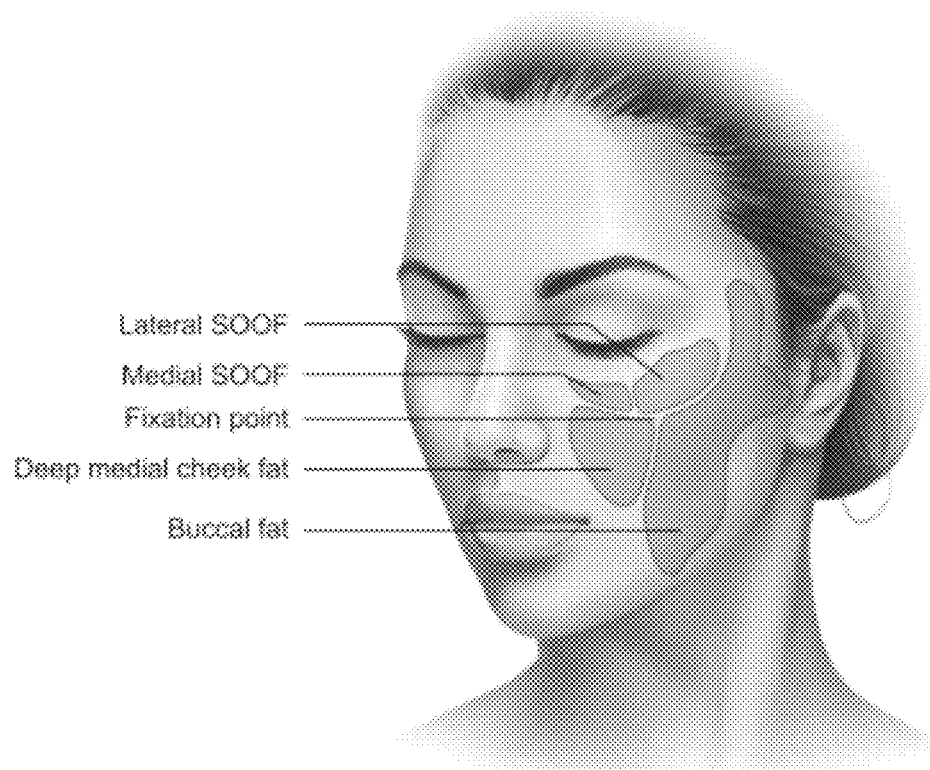
FIG. 7 illustrates deep fat pads of a human face according to the prior art.

The present technique (sometimes referred to herein and by the present applicant as "Cheek Pop" for convenience and identification of origin) is different from traditional methods of PDO thread insertion for face lifting. The present thread lifting technique employs an inferior-to-superior method of thread insertion, as opposed to the traditional superior-to-inferior method of thread insertion. Instead of inserting and burying the thread into the temporal fascia or lateral face and angling the vectors downward in conventional thread-lifting procedures (see FIG. 1), the present vectors are inserted and angled upward and inward (see FIG. 16). Another distinction is the tissue plane and depth of the present thread lifting technique uses for its effect. As opposed to insertion in the superficial fat pads (see FIG. 6), the present invention targets the deep fat pads (see FIG. 7), such as the buccal fat pad, deep medial cheek fat pad, and/or the sub-orbicularis oculi fat. Thread placement was confirmed with a cadaver specimen dissection employing the present technique. There are currently no other documented thread lifting techniques inserting into the deep facial fat pads or carried out as described herein.

Figure 8:
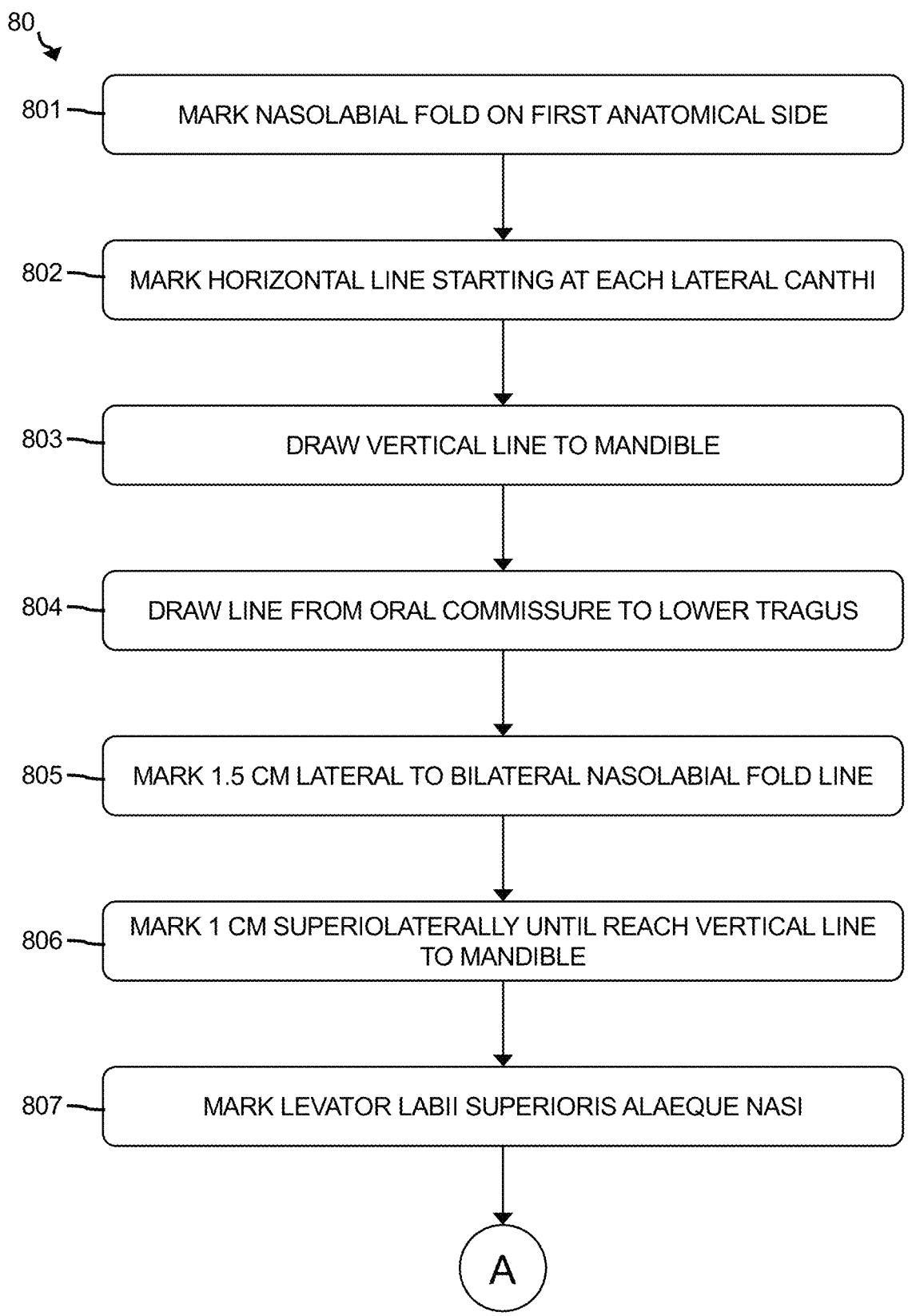
FIG. 8 is a flow chart of a method for marking a face to perform a Cheek Pop thread lifting technique according to an embodiment.
Figure 8:
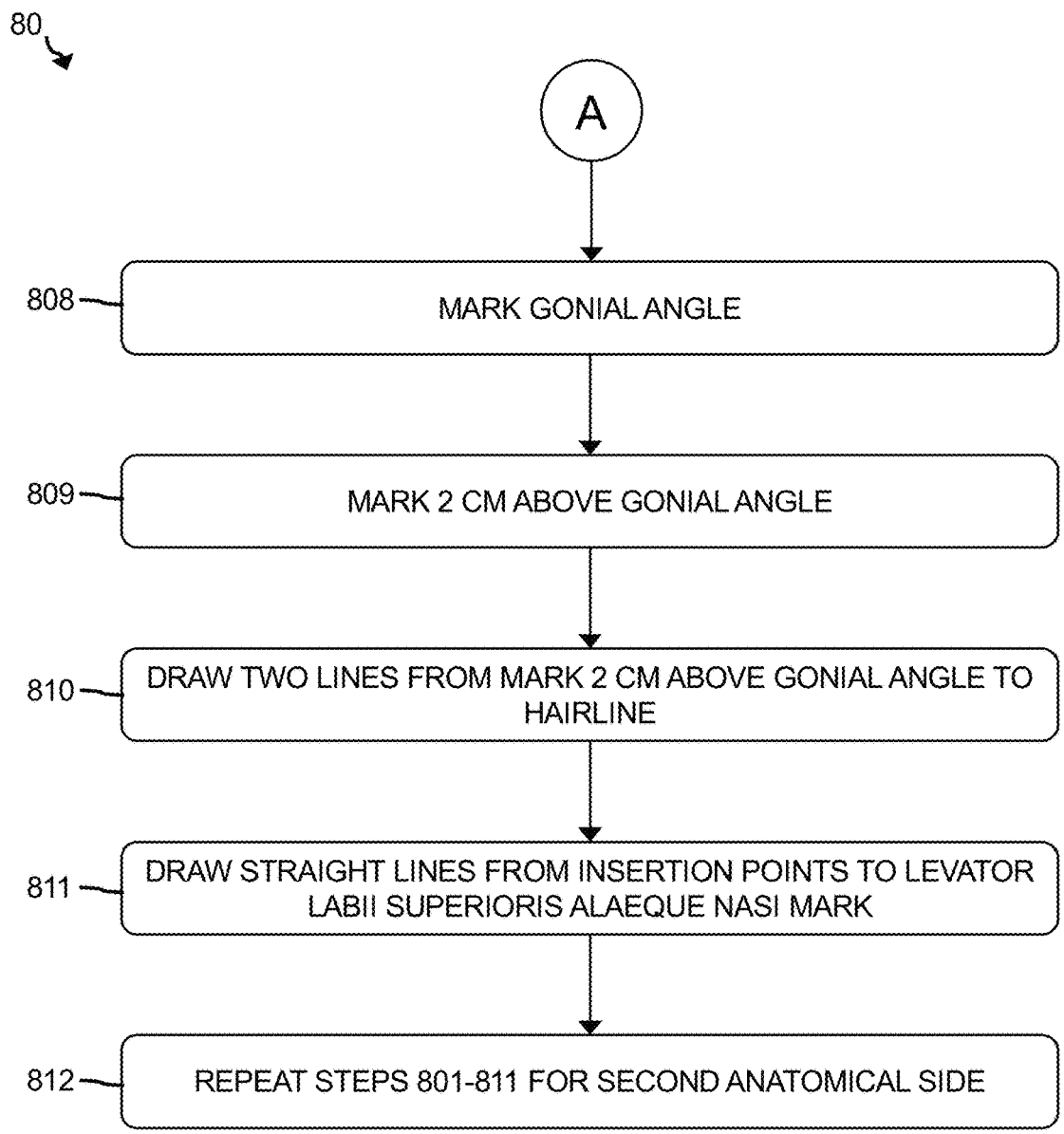

FIG. 8 is a flow chart of a method 80 for marking a face to perform the present thread lifting technique according to an embodiment. The face can be marked with a surgical marking pen or another technique.

Figure 9:
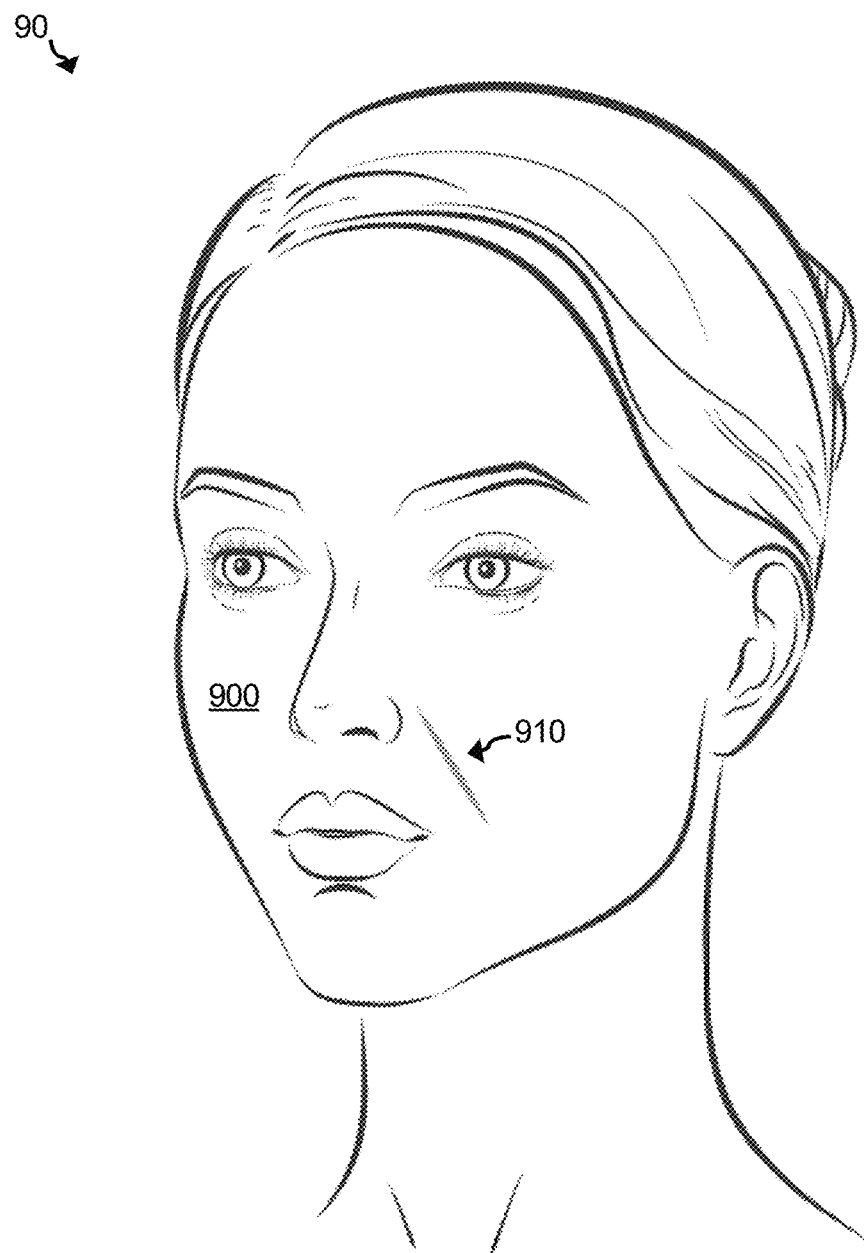
FIGS. 9-16 illustrate a human face marked according to the method illustrated in FIG. 8.

In step 801, the nasolabial fold on a first anatomical side of the patient's face is marked. An example of a marked nasolabial folds line 910 on the left anatomical side 902 (e.g., a first anatomical side) of the face 900 of a subject 90 is illustrated in FIG. 9. This step would be repeated for the right anatomical side 904 (e.g., a second anatomical side) of the face 900 of a subject 90.

In step 802, a horizontal line on the first anatomical side of the patient's face is drawn starting at the lateral canthus. The horizontal line is preferably 2 cm in length but can be greater than 2 cm. All dimensions given herein should be understood to be given by way of example and not by way of limitation. A particular instance of the invention and/or subject may call for varying dimensions as would be appreciated by those skilled in the art. When a quantitative parameter or dimension is given in an example embodiment, it may thus be considered approximate or about that value, which can comprehend values near the stated value (e.g., plus or minus ten percent thereof in some examples, or plus or minus twenty percent thereof in other examples). The specific parameter or dimension at hand would guide those skilled in the art as to how nearly the same a variation thereof might be in a given case.

In step 803, a vertical line on the first anatomical side of the patient's face is drawn straight down to the mandible from the from horizontal line drawn in step 802. The vertical line is preferably drawn from the point on the horizontal line that is about 2 cm from the lateral canthi, which is the end of the horizontal line when the horizontal line is about 2 cm in length.

Figure 10:
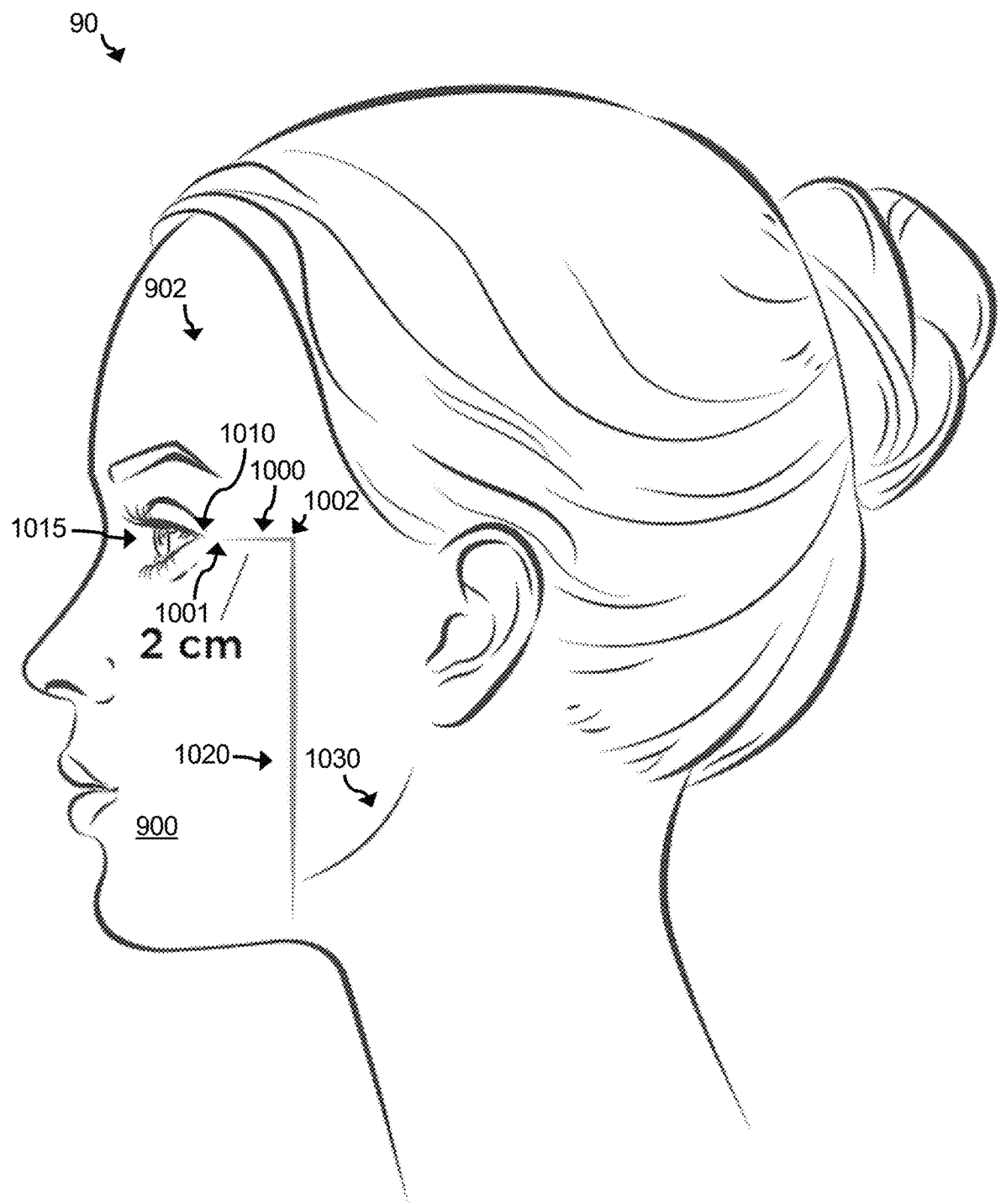

An example of a horizontal line 1000 starting at a lateral canthus 1010 of the subject is illustrated in FIG. 10. If extended, the horizontal line 1000 would approximately or substantially bisect the eye 1015 of the subject 90. This figure also illustrates a vertical line 1020 that extends from the horizontal line 1000 to the mandible 1030. The vertical line 1020 begins about 2 cm along the horizontal line 1000 from the lateral canthus 1010, which is at the beginning 1001 of the horizontal line 1000. When the horizontal line 1000 is about 2 cm in length, the vertical line 1020 begins at the end 1002 of the horizontal line 1000.

Figure 11:
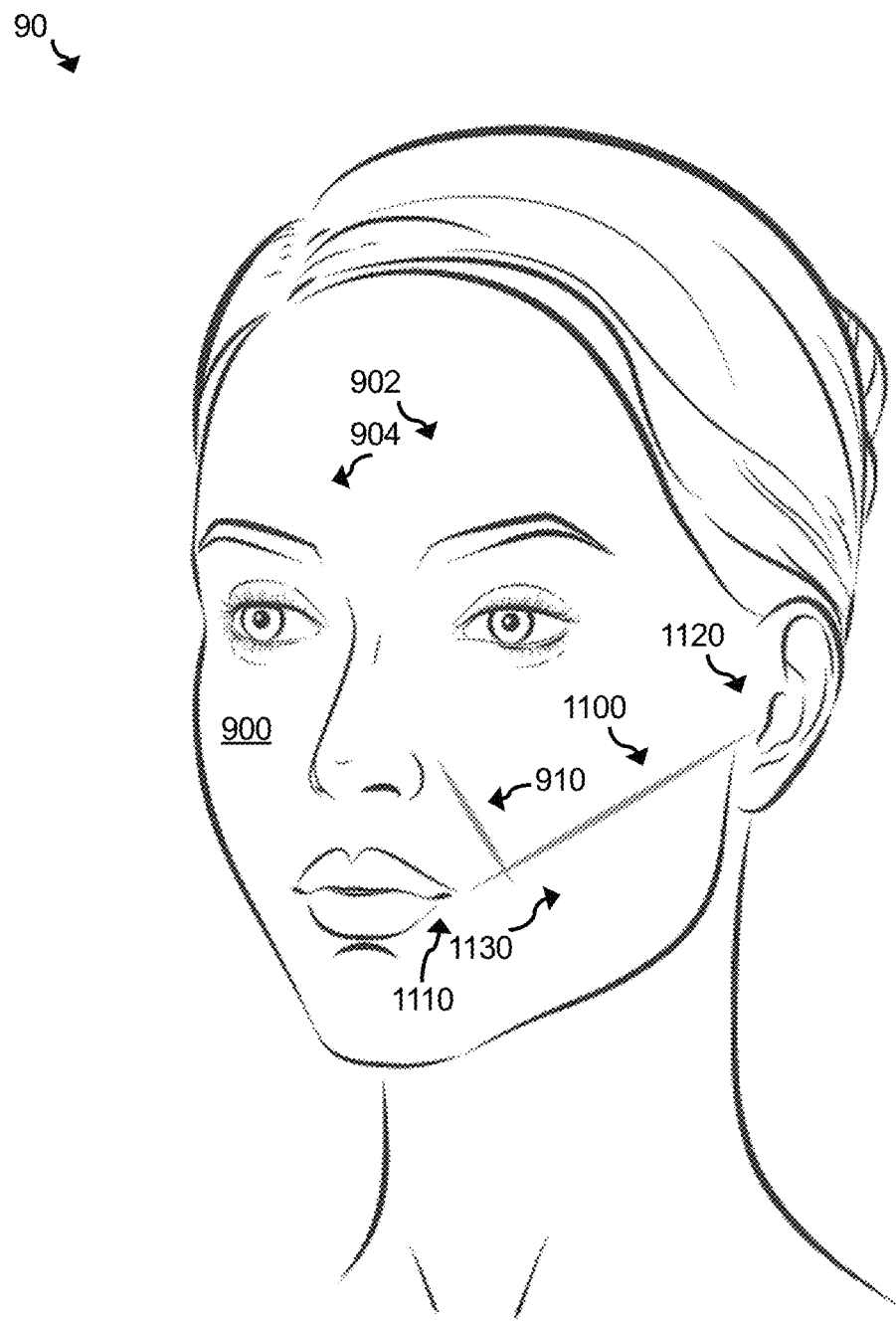

In step 804, a line is drawn on the first anatomical side of the patient's face from the oral commissure to the lower tragus of the subject. This line can be used to identify and/or can represent the natural submalar contour line. An example of a line 1100 drawn from the oral commissure 1110 to the lower tragus 1120 is illustrated in FIG. 11. The submalar contour shadow 1130 is located just below line 1100. Line 1100 can intersect marked bilateral nasolabial folds line 910 at intersection point 1102.

Figure 12:
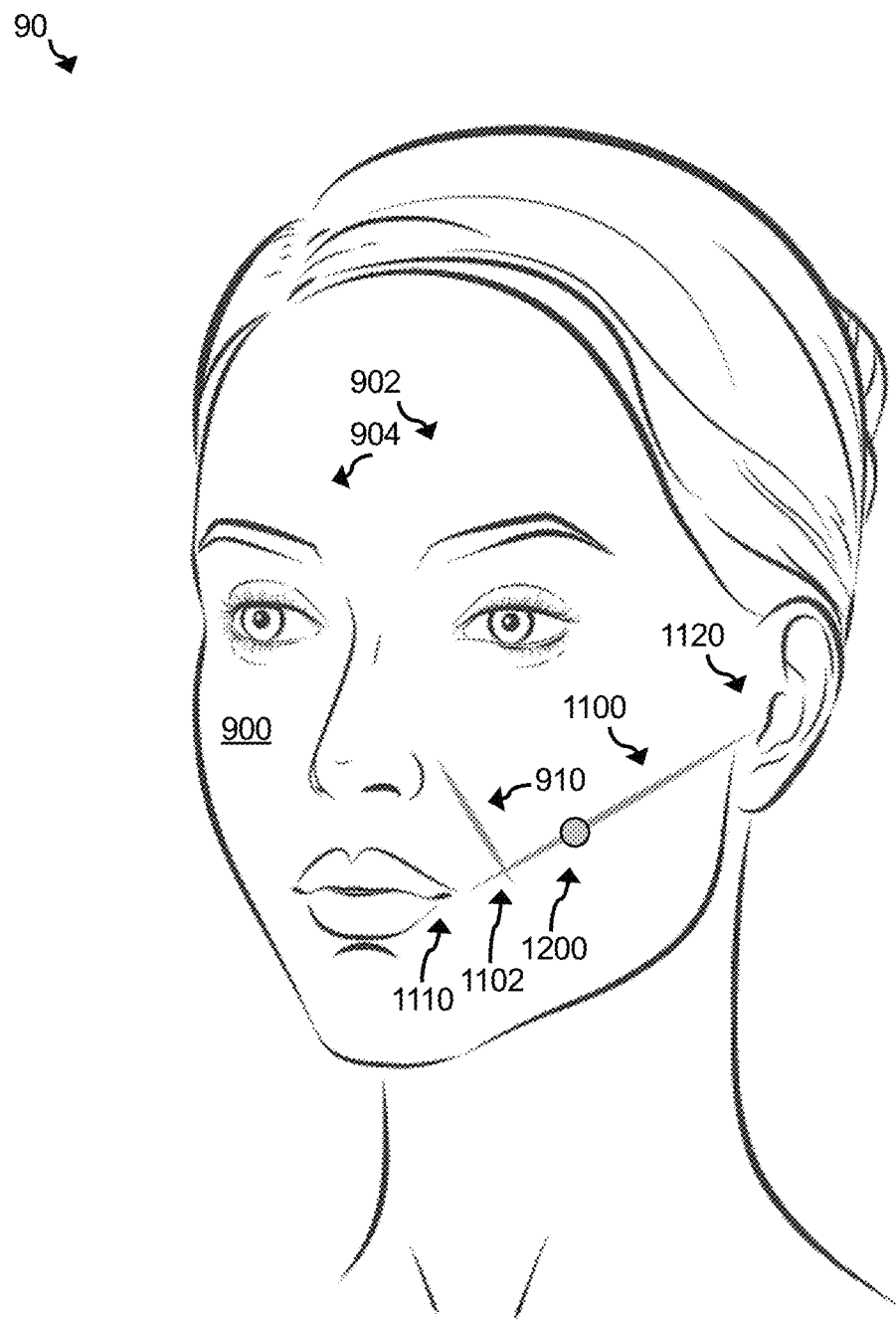

In step 805, a mark on the first anatomical side of the patient's face is made about 1.5 cm lateral to each bilateral nasolabial fold line made in step 801. An example of a mark 1200 made about 1.5 cm lateral to the bilateral nasolabial folds line 910 is illustrated in FIG. 12. The mark 1200 is made along line 1100. Mark 1200 represents the first insertion point in the present thread lifting technique. In an aspect, care should be taken to measure mark 1200 to avoid inserting into the nasolabial fat pad, which would cause an unnatural result.

Figure 13:
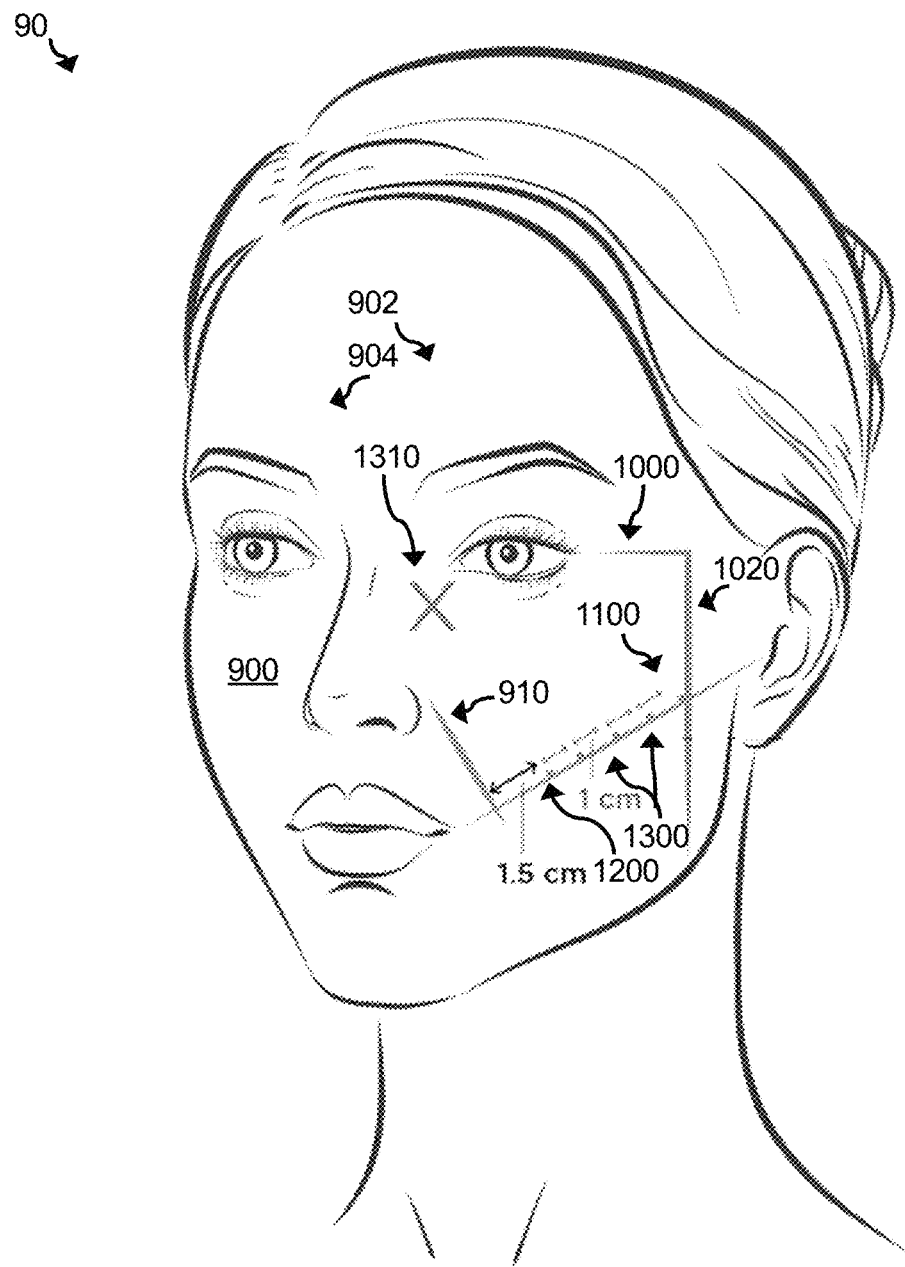

In step 806, a series of marks on the first anatomical side of the patient's face are made at about 1 cm intervals moving superiolaterally along the submalar shadow from the mark made in step 805. The marks are made until the vertical line to the mandible (formed in step 803) is reached. An example of the marks 1300 made in this step is illustrated in FIG. 13.

Marks 1300 can be made in several ways according to embodiments of the invention. In one example, the index finger is placed and pointed downward along the submalar contour (e.g., along line 1100), lined up just inferior to the first dot (e.g., mark 1200), with the fingernail pointed to the corner of the mouth. Alternatively, a straight edge or a straight device, such as a tongue depressor, can be used. Use the index finger (or tongue depressor) as a guide to ensure the dots (e.g., marks 1300) stay in a level line in the submalar shadow. Another dot or mark (e.g., marks 1300) is made about 1 cm lateral to the first dot, moving superiolaterally along the submalar shadow. Additional dots or marks (e.g., marks 1300) are made until the vertical line 1020 to the mandible is reached. There should preferably be between 4-7 dots (mark 1200 and marks 1300), depending on the width of the patient's face, but again, those skilled in the art will understand how to adapt the invention to a given application and subject. The marks 1200, 1300 represent insertion points in the present thread lifting technique.

In step 807, the levator labii superioris alaeque nasi on the first anatomical side of the patient's face is marked, such as with a small "X" or other indication or mark. The levator labii superioris alaeque nasi is located skin just inferior to the tear trough, which is just lateral the border of the upper nose. An example mark 1310 on the levator labii superioris alaeque nasi is illustrated in FIG. 13.

Figure 14:
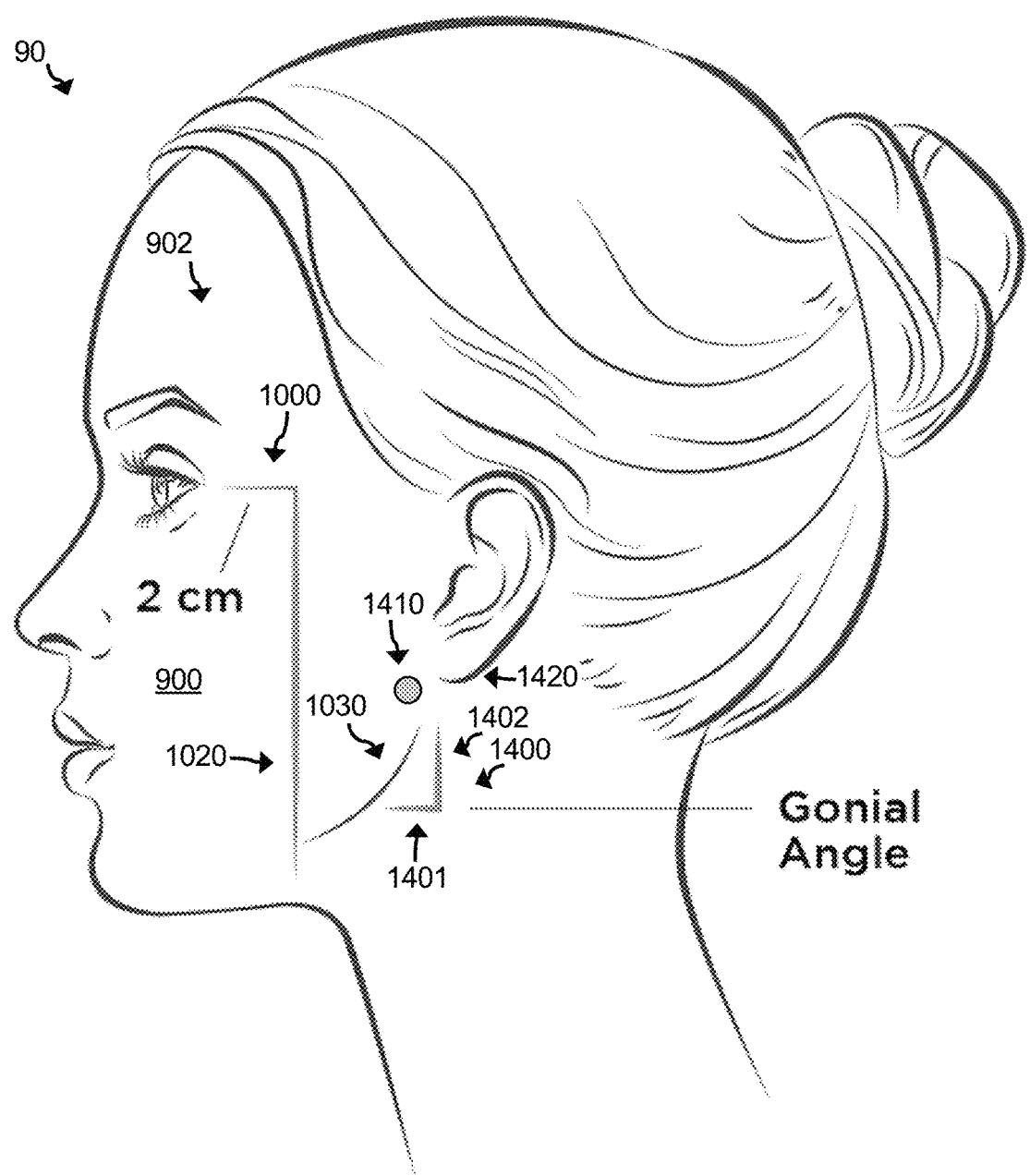

In step 808, the gonial angle on the first anatomical side of the patient's face is marked. The index and middle finger can press inward and cup the angle of the mandible (gonial angle) prior to marking the gonial angle. An example marking 1400 of the gonial angle is illustrated in FIG. 14. The marking 1400 includes orthogonal horizontal and vertical lines 1401, 1402.

In step 809, a mark on the first anatomical side of the patient's face is made about 2 cm above the gonial angle marking in step 808. The mark is anterior to the earlobe. An example marking 1410 about 2 cm above the marking 1400 of the gonial angle is illustrated in FIG. 14. Marking 1410 is anterior to earlobe 1420. Marking 1410 represents another insertion point in the present thread lifting technique.

Figure 15:
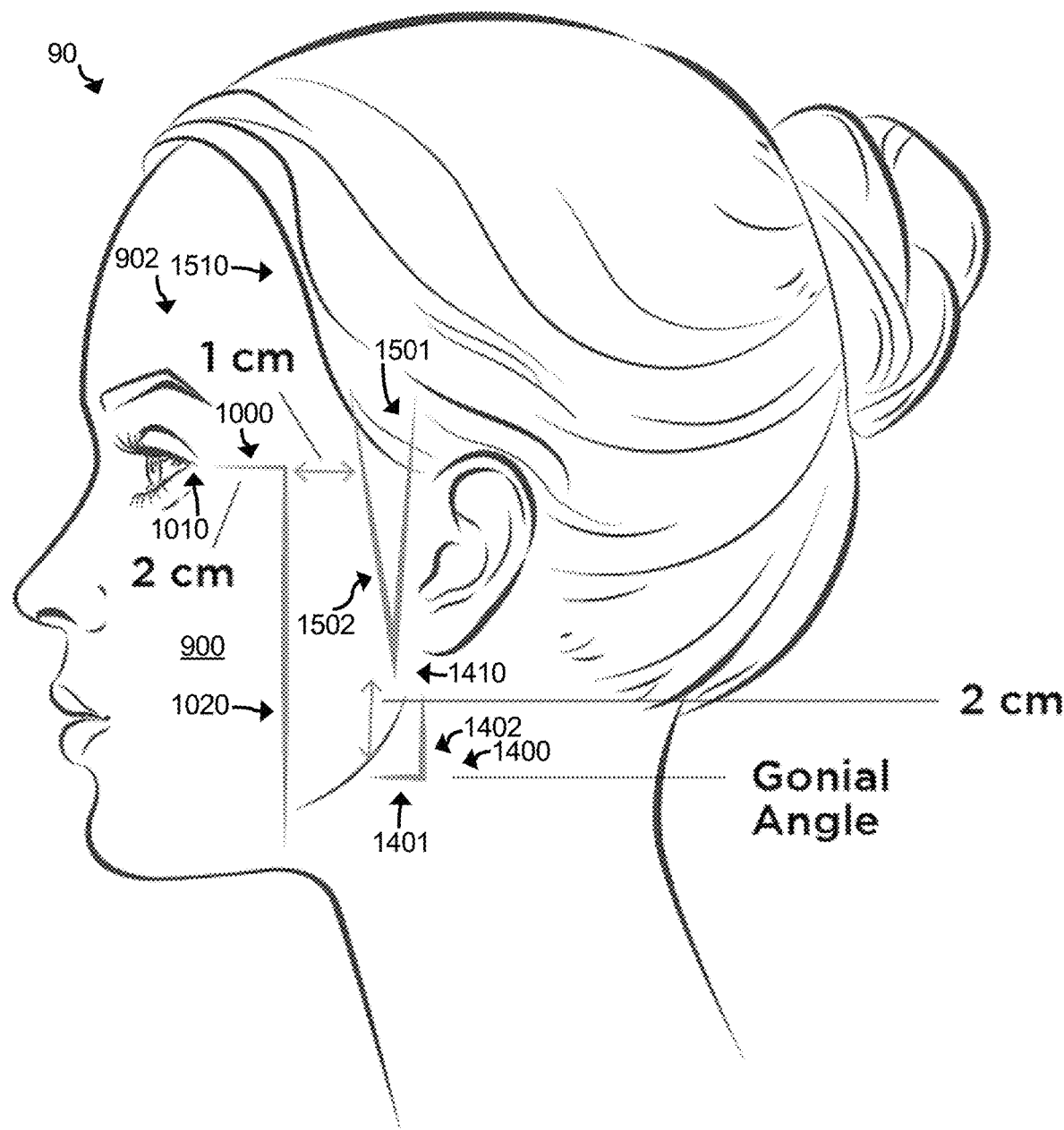

In step 810, two lines are drawn on the first anatomical side of the patient's face from the mark made in step 809. A first line is drawn going straight up to the hairline, staying about 1 cm from the tragus. A second line is drawn just medial to the first line and angled to the hair line. Example first and second lines 1501, 1502 are illustrated in FIG. 15. Each line 1501, 1502 begins at marking 1410. The first line 1501 extends from the marking 1410 to the hairline 1510 and is approximately parallel to (e.g., within 10° of and/or within 5° of) line 1402 and/or to line 1020 and is approximately orthogonal to horizontal lines 1000, 1401. The second line 1502 extends from the marking 1410 to the hairline 1510 and is medial to the first line 1501. The second line 1502 is about 1 cm lateral to the vertical line 1020 when measured along horizontal line 1000, which is aligned with the lateral canthus 1010. Lines 1501, 1502 represent gonial angle insertion vectors in the present thread lifting technique. The portion of lines 1501, 1502 proximal to the hairline 1610 represent the end point of each insertion vector (lines 1501, 1502).

Figure 16:
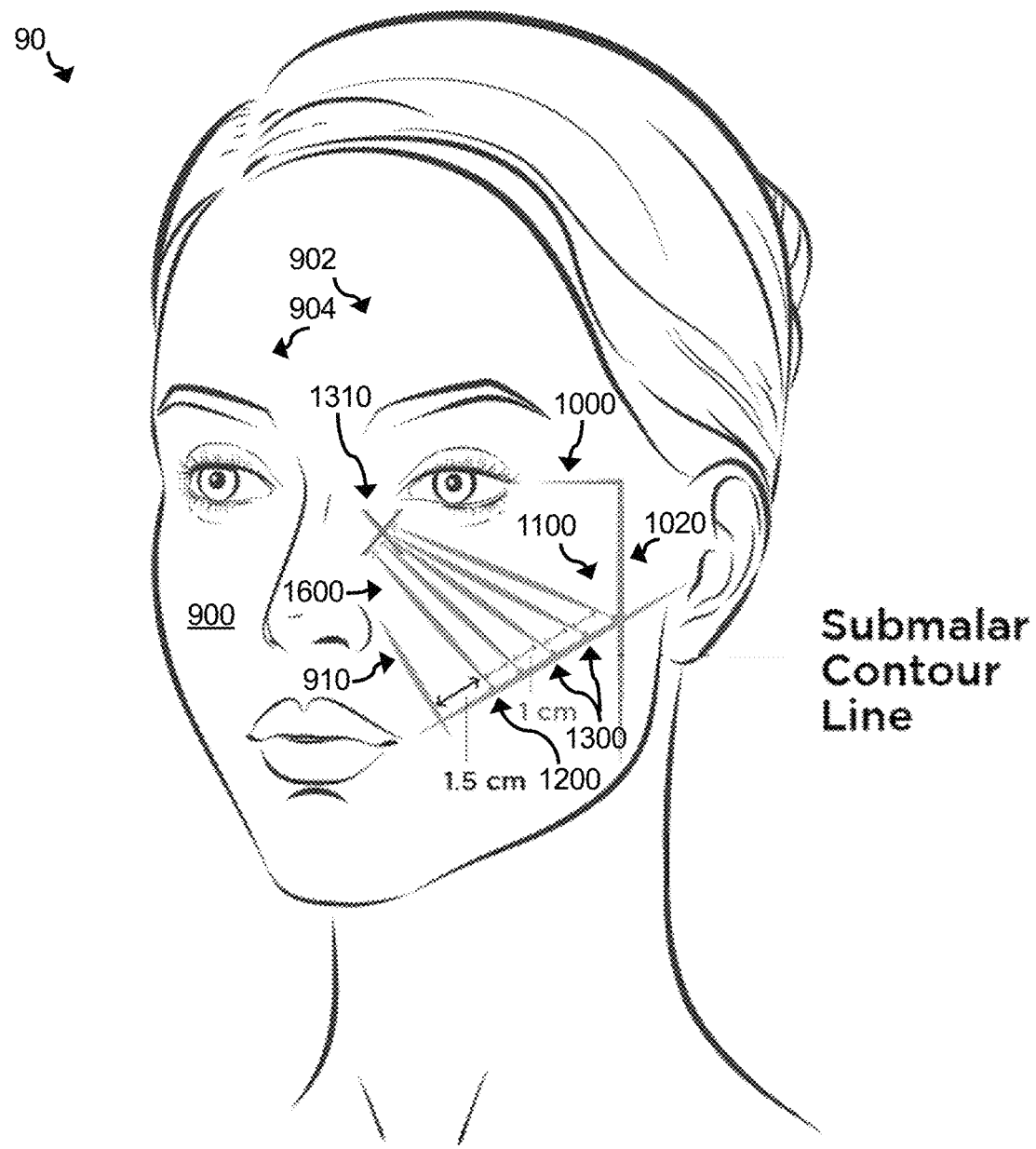

In step 811, straight lines on the first anatomical side of the patient's face are drawn from each insertion point (marked in steps 805 and 806) to the levator labii superioris alaeque nasi mark (made in step 807). An example of the straight lines 1600 drawn from each insertion point 1200, 1300 to mark 1310 is illustrated in FIG. 16. The straight lines 1600 represent insertion vectors in the present thread lifting technique. Mark 1310 represents the end point of each insertion vector (straight line 1600). Step 811 can be optional in some embodiments.

In step 812, the marks and lines made in steps 801-811 are repeated for the second anatomical side (e.g., anatomical right side 904) of the patient's face.

Figure 17:
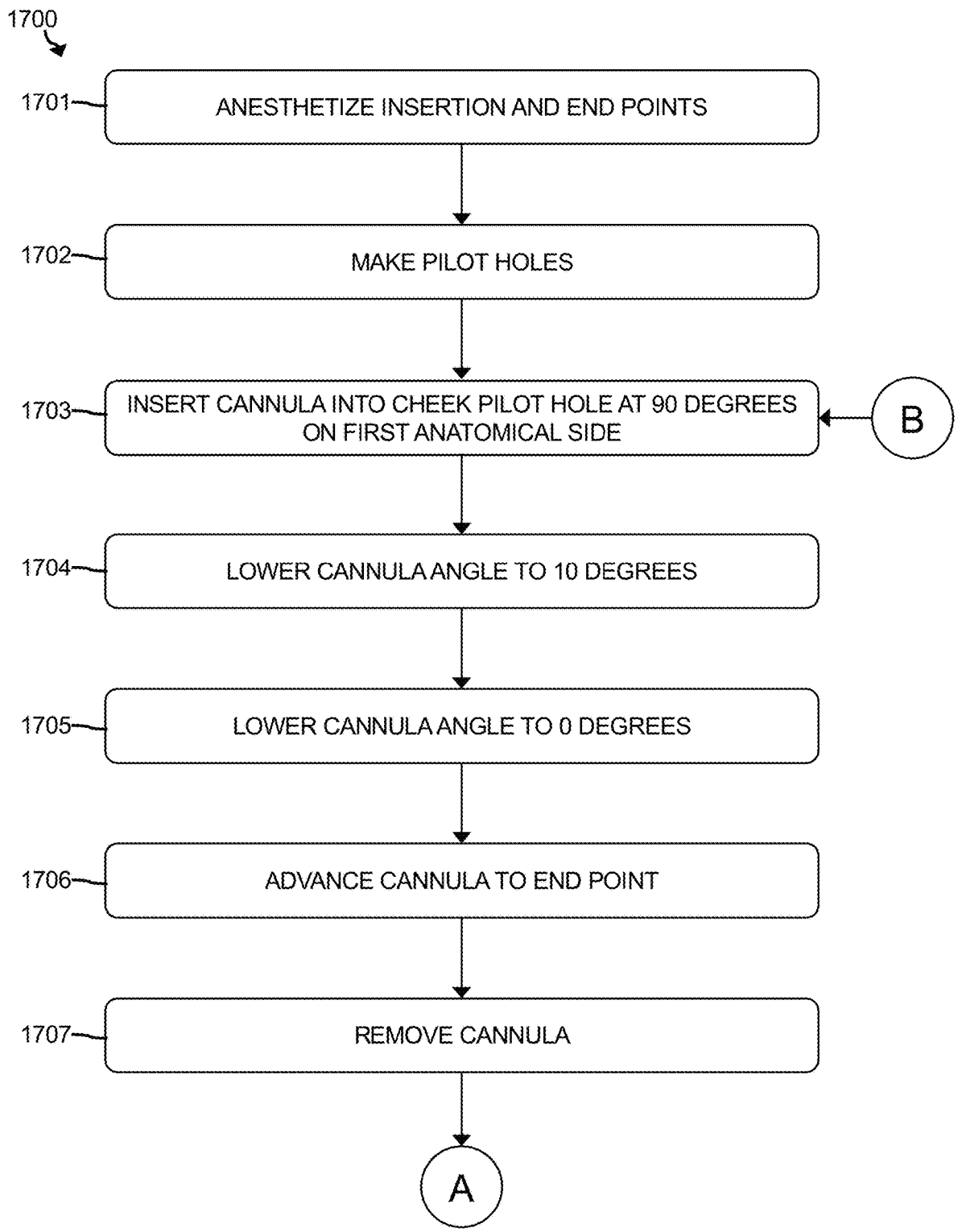
FIG. 17 is a flow chart of a method for performing the Cheek Pop thread lifting technique according to an embodiment.
Figure 17:
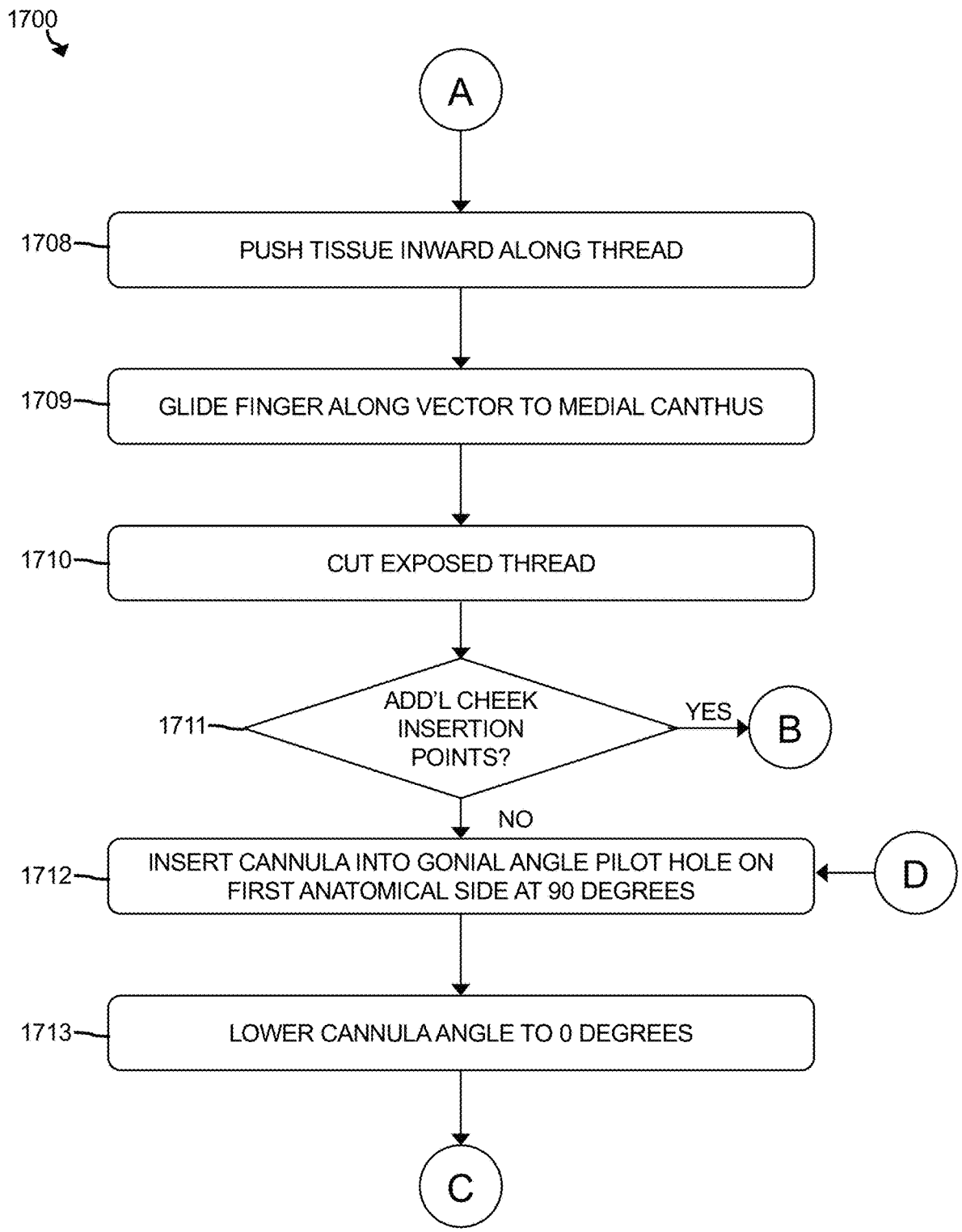
Figure 17:
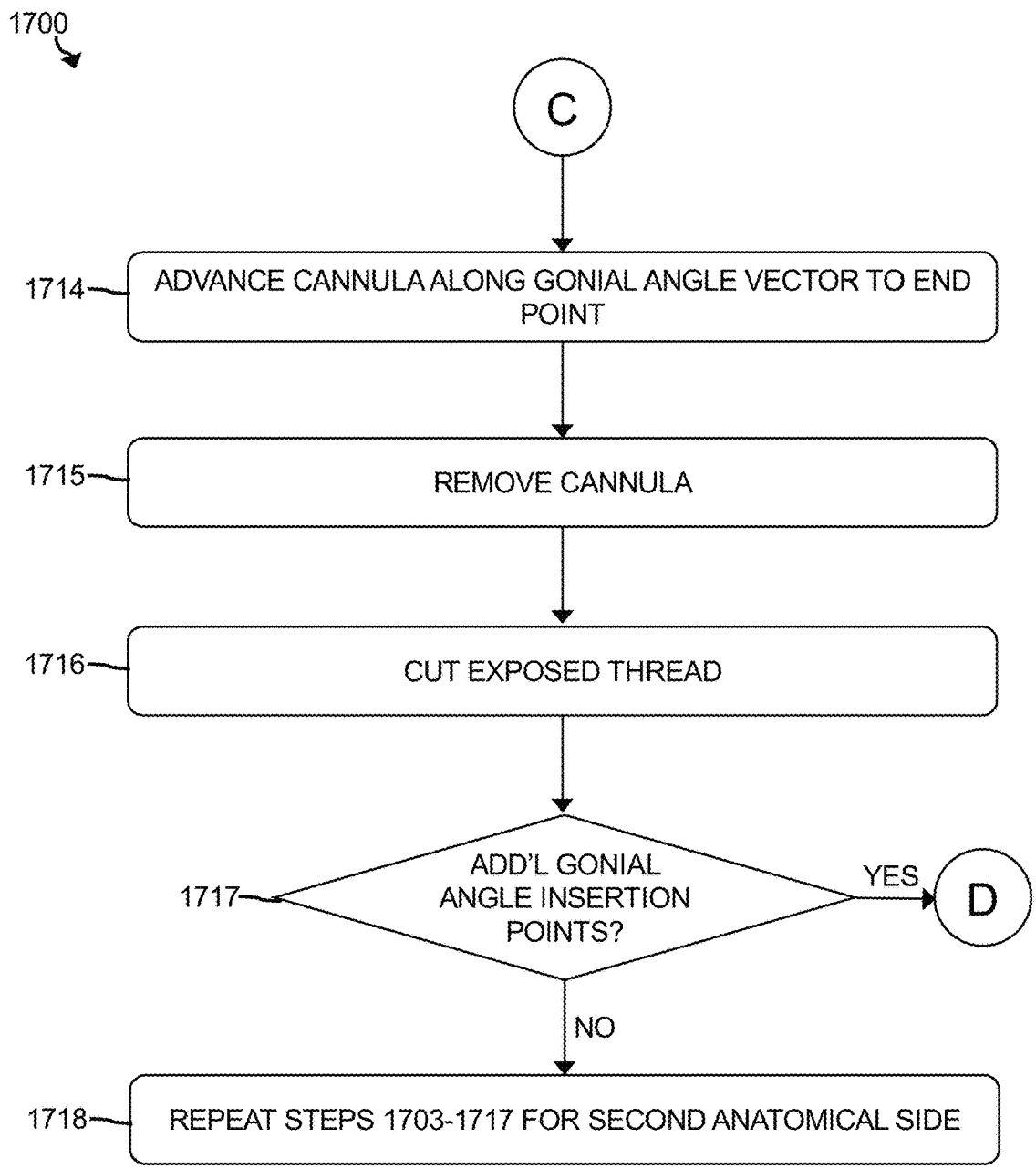

After the face is marked (e.g., in method 80), the face is ready for the procedure. FIG. 17 is a flow chart of a method 1700 for performing the present thread lifting technique according to an embodiment.

In step 1701, the insertion and end points of the insertion vectors are anesthetized. Preferably, 0.3 ml of 2% lidocaine at each insertion point and at each end point is used to anesthetize. For example, the insertion points represented by markings 1200, 1300, 1410 and the end points represented by marking 1310 and hairline 1510 are anesthetized.

In step 1702, pilot holes are made at each insertion point (e.g., at markings 1200, 1300, 1410) on each anatomical side of the patient. The pilot holes are preferably made with an 18-gauge needle or a similar device as would be appreciated by those skilled in the art. The non-dominant hand can be used to gently squeeze around each insertion point to ease the insertion of the pilot needle. With the bevel upward, pierce into the skin at the marked site at approximately a 45-degree angle, just past the bevel, to form the pilot hole.

In step 1703, a cannula is inserted into one of the pilot holes on the cheek (i.e., a pilot hole at marking 1200 or 1300) on the first anatomical side (e.g., anatomical left side 902) of the patient. The cannula is preferably a 19-gauge L-shaped cannula with a 100 mm multi-directional laser cut PDO thread. The cannula is inserted into the pilot hole at about a 90-degree angle with the cannula bevel up, angled toward the medial canthus. The 90-degree angle is defined between an axis of the cannula and a surface of the skin such that the axis of the cannula is approximately orthogonal to the skin surface. A twisting motion back and forth may be necessary to get in and past the subdermal layer. Once the cannula is inserted approximately 3-5 mm deep, in step 1704 the angle of the cannula is lowered to approximately 10 degrees continuing the vector toward the medial canthus. The cannula is then advanced by about 1 cm at 10 degrees. Once the cannula is advanced by approximately 1 cm at 10 degrees, it should be inferior to the SMAS and zygomaticus muscle into a deep cheek fat pad (e.g., the buccal fat pad, deep medial cheek fat pad, and/or the sub-orbicularis oculi fat pad).

Figure 18:
FIG. 18 illustrates an L-shaped cannula and a multi-directional laser cut PDO thread that can be used to perform the method illustrated in FIG. 17.
Figure 19:
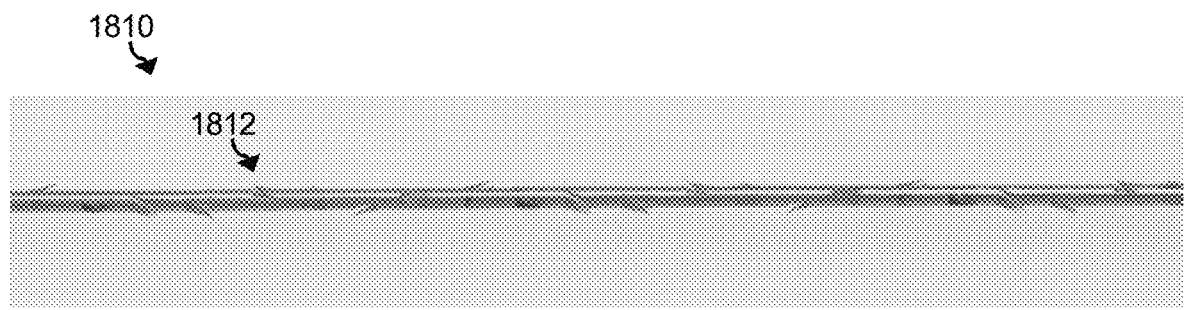
FIG. 19 is a detailed view of the multi-directional laser cut PDO thread illustrated in FIG. 18.
Figure 20:
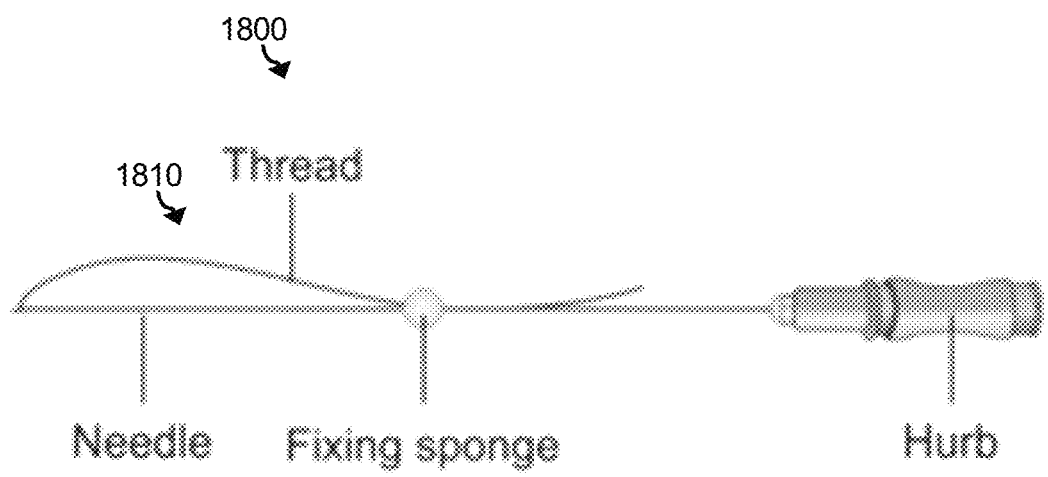
FIG. 20 is an example functional diagram of the multi-directional laser cut PDO thread and L-shaped cannula illustrated in FIG. 18.

An example of an L-shaped cannula 1800 is illustrated in FIG. 18. L-shaped cannula 1800 preferably has a blunt tip 1802 at the insertable or distal end. The cannula 1800 can be 21-gauge to 18-gauge depending on the patient. In an embodiment, the cannula 1800 is preferably 18-gauge. A multi-directional laser cut PDO thread 1810 is contained in the cannula 1800. The thread 1810 includes barbs 1812 at 360 degrees around the perimeter of the thread 1810 and oriented in both directions (e.g., proximally and distally), for example as illustrated in FIG. 19. Using cannula 1800 can reduce or minimize bleeding, while the shape of the distal tip 1802 allows easier passage through the layers of tissue required for the present procedure. An example functional diagram of the thread 1810 within the cannula 1800 is illustrated in FIG. 20.

Figure 21:
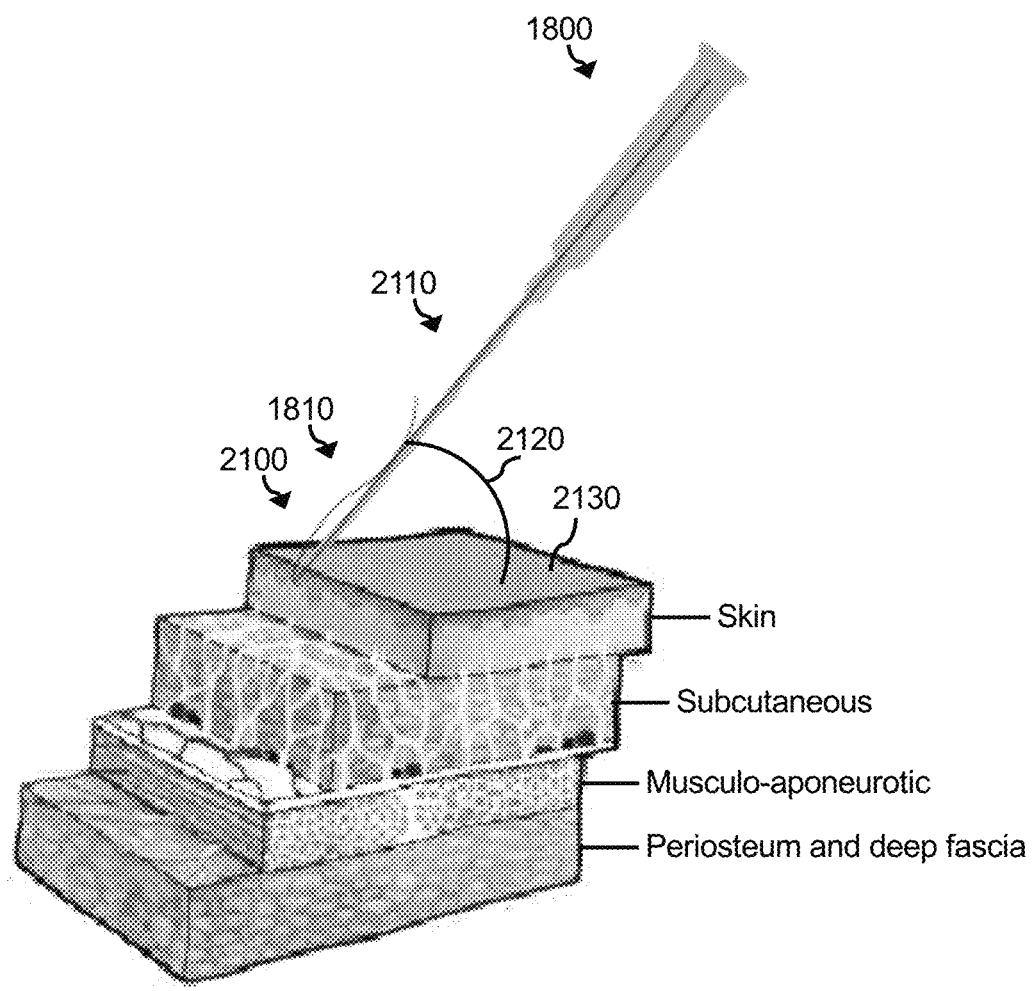
FIGS. 21-25 are example illustrations of certain steps in the flow chart illustrated in FIG. 17 according to an embodiment.

FIG. 21 is an example illustration of step 1702 where a pilot hole 2100 is formed on the skin of the subject. The pilot hole 2100 is formed with a needle 2110, such as an 18-gauge needle. The needle 2110 can be attached to the cannula 1800 which can include thread 1810. The pilot hole 2100 is formed with the needle 2110 oriented at approximately a 45-degree angle 2120 with respect to the skin surface 2130 and the needle 2110 (e.g., with respect to a plane defined by the skin surface 2130).

Figure 22:
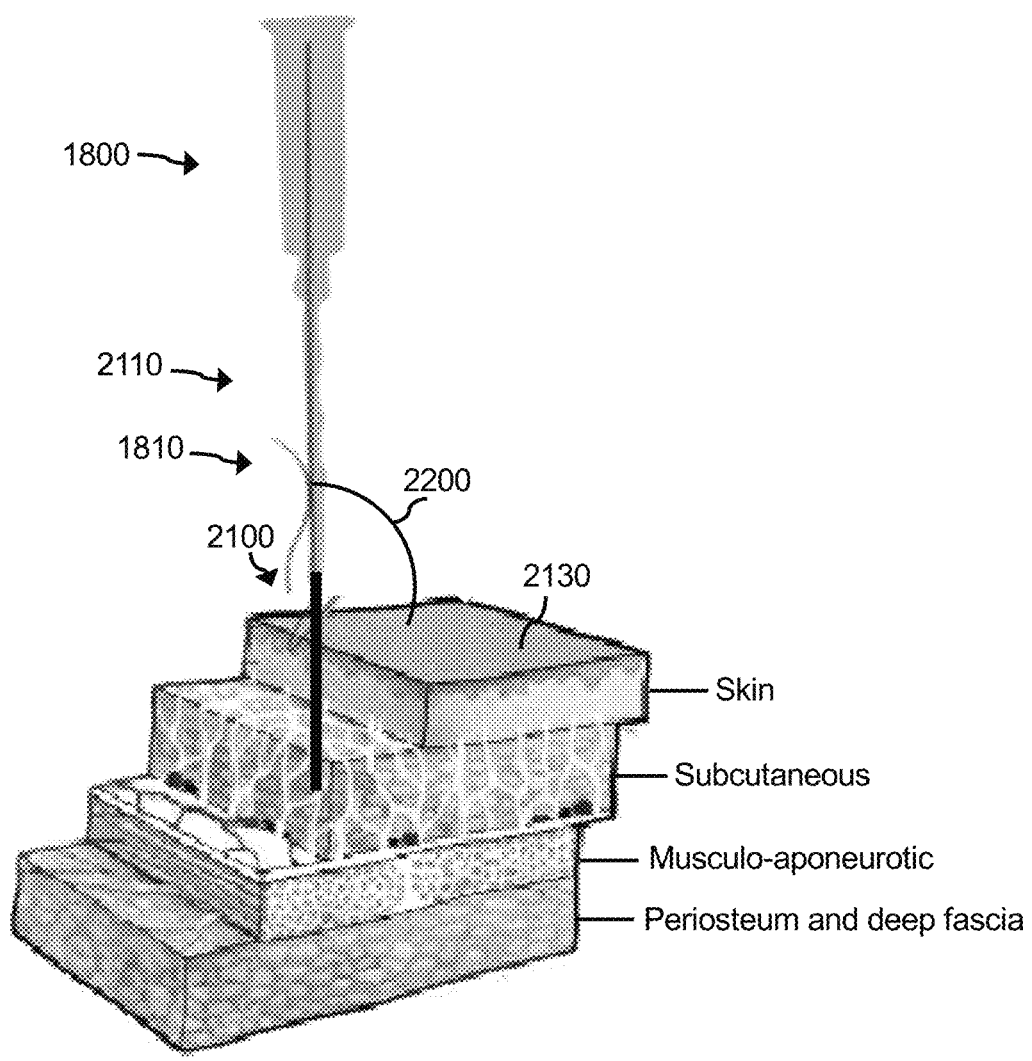

FIG. 22 is an example illustration of step 1703 where the needle 2110 of the cannula 1800 is inserted into the pilot hole 2100 at about a 90-degree angle 2200 with respect to the skin surface 2130 (e.g., with respect to a plane defined by the skin surface 2130) and the needle 2110. The needle 2110 is inserted 3-5 mm deep into the subcutaneous layer.

Figure 23:
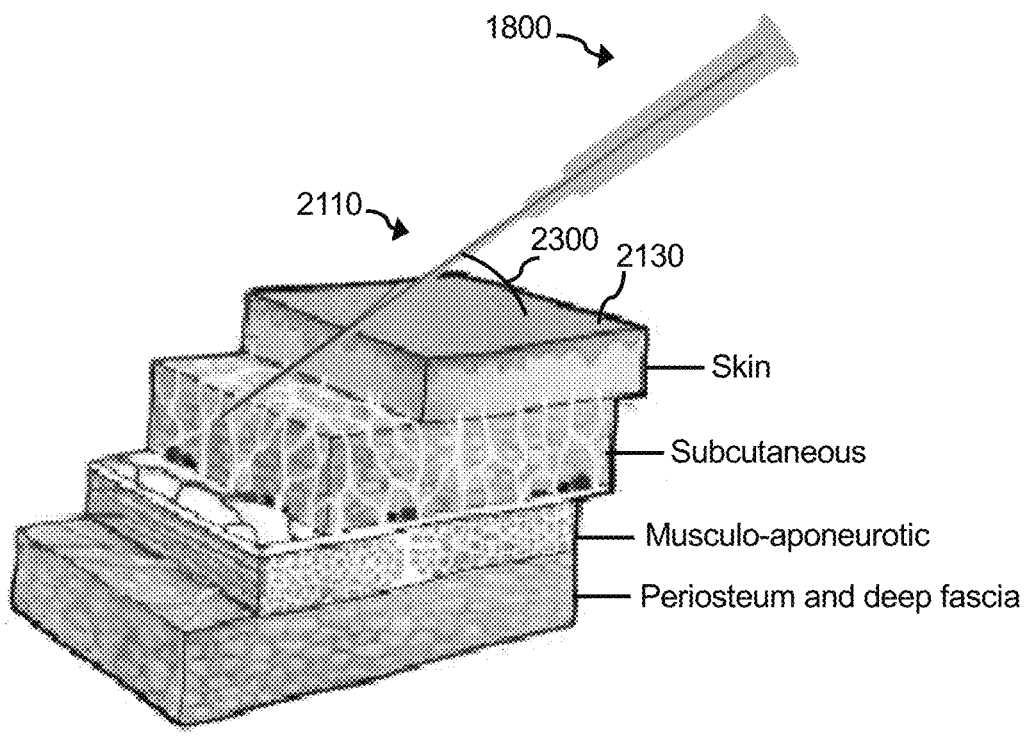

FIG. 23 is an example illustration of step 1704 where the needle 2110 of the cannula 1800 is lowered to approximately a 10-degree angle 2300 with respect to the skin surface 2130 (e.g., with respect to a plane defined by the skin surface 2130). The needle 2110 is then advanced by about 1 cm at the 10-degree angle 2300.

In step 1705, the angle of the cannula is lowered to about 0 degrees, parallel to the skin surface. The non-dominant hand can optionally pinch the skin around the insertion point as necessary to gently advance the cannula. Additionally, or alternatively, the skin inferior to the cannula can be rotated gently back and forth and pulled the onto the cannula to advance the cannula. Unlike traditional thread lifting in the subcutaneous plane where you can clearly feel the cannula outline under the skin, in the present technique an operator may not feel any distinct delineation of the cannula under the skin when properly seeded in the deep fat pads. Instead, an operator may feel and may even see the tissue obscurely being lifted upward, without any distinct feel or sight of the outline of the cannula.

In step 1706, the cannula is advanced at 0 degrees to the end point (e.g., to marking 1310 of the levator labii superioris alaeque nasi) through the deep cheek fat pads (e.g., the buccal fat pad, deep medial cheek fat pad, and/or the sub-orbicularis oculi fat pad). Once the cannula reaches the end point "X" (e.g., marking 1310), we stop advancing and push the tissue upward along that vector. If a 100 mm cannula device was used, as an example, the entire length of the cannula may not be used. The distal thread is being anchored into the fascia of the levator labii superioris alaeque nasi.

Note that while the endpoint of all threads is on the X (e.g., marking 1310), the vectors with more inferior insertion points will angle to the lower part of the X, while the more superior vectors will be angled to the upper part of the X, as illustrated in FIG. 16. Of course, other markings or indications can be substituted for those given here by way of example, and this substitution would be comprehended by this disclosure and invention, as would the afore-mentioned variations in the example dimensions, angles and other quantitative parameters.

Figure 24:
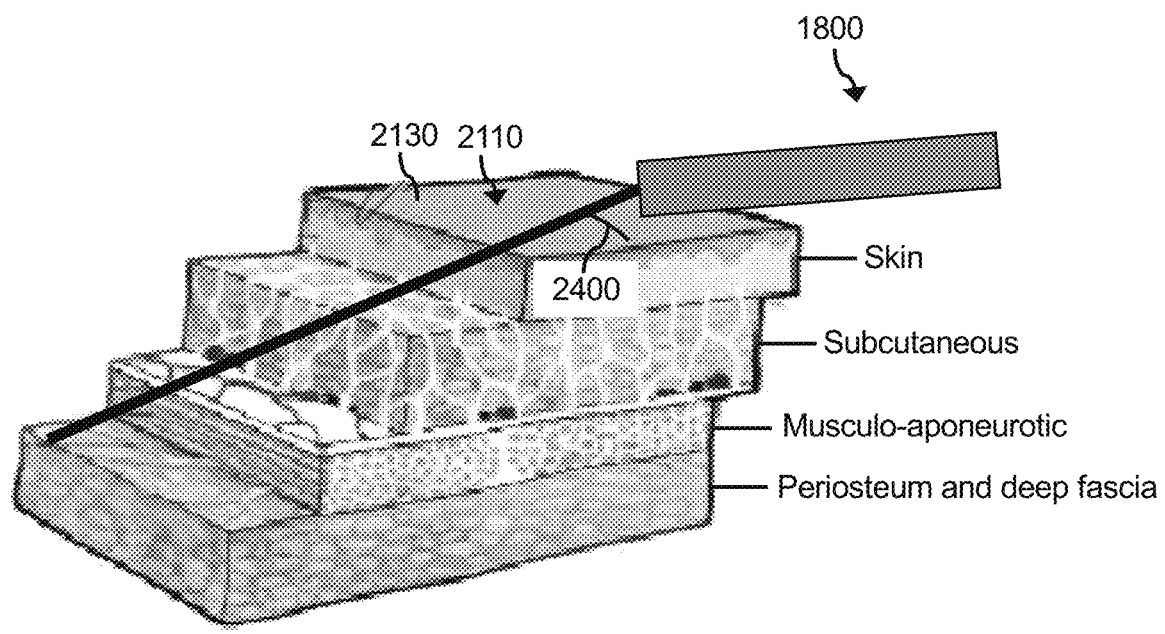

FIG. 24 is an example illustration of steps 1705 and 1706 where the needle 2110 of the cannula 1800 is lowered to approximately a 0-degree angle 2400 with respect to the skin surface 2130 (e.g., with respect to a plane defined by the skin surface 2130). The needle 2110 is then advanced by about 1 cm at the 10-degree angle 2300.

Figure 25:
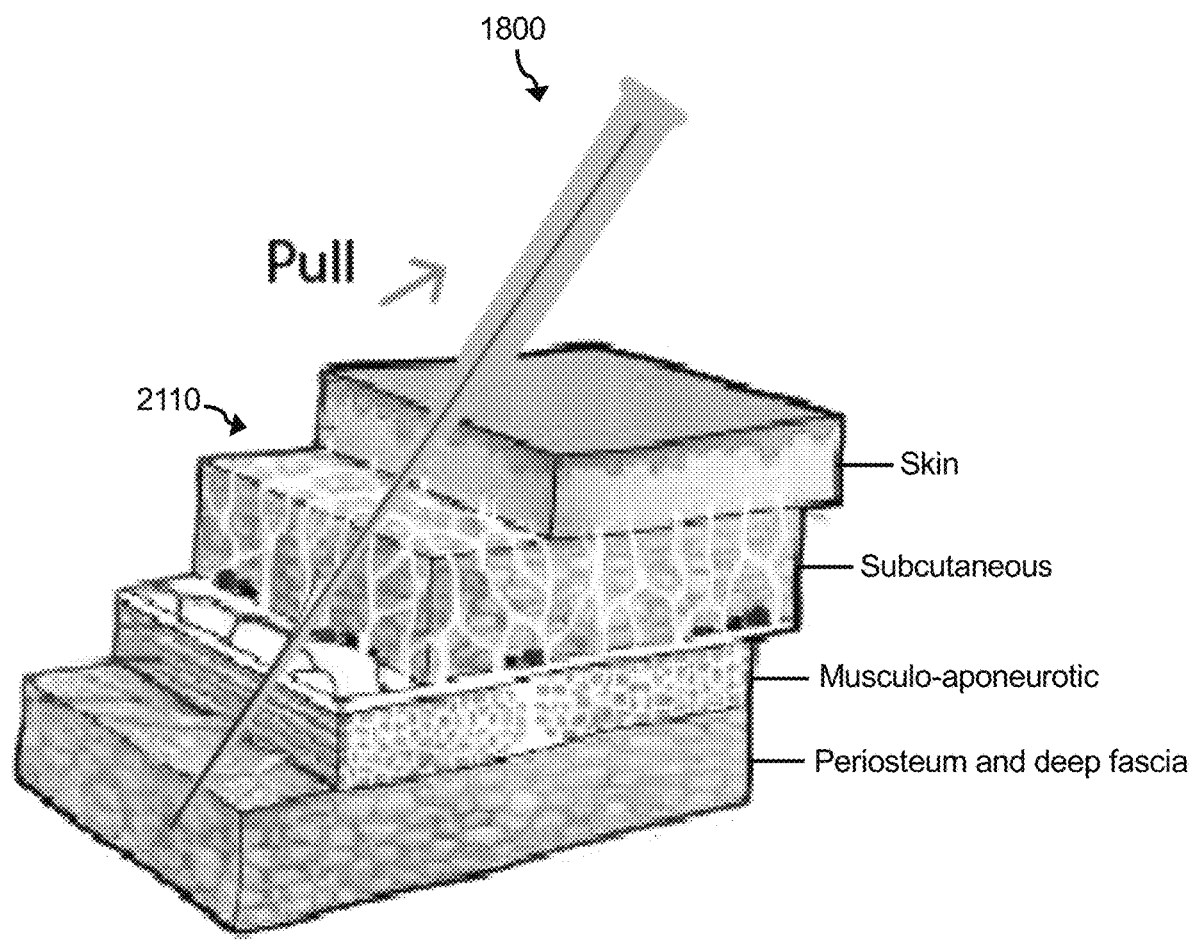

FIG. 25 is an example illustration of steps 1706 and 1707 where the needle 2110 of the cannula 1800 has reached the end point "X" (e.g., marking 1310), the tissue is pushed upward along the vector, and then the needle 2110 is removed.

In step 1707, the cannula is removed from the cheek insertion point. As the cannula is removed, the cannula is preferably rotated 360 degrees (clockwise or counter-clockwise) preferably more than one full rotation (e.g., 3-5 times) upon exit, while simultaneously pressing the skin upward along the direction of the vector. The thread will be left in place with a visible dimpling present at the insertion site. This step suspends the deep fat pads in an elevated position.

In step 1708 (via placeholder A), the tissue is pushed inwardly along the thread, further accentuating a dimple. The tissue can be pushed inwardly with gentle pressure using the non-dominant thumb and index finger.

In step 1709, the finger (e.g., the index finger of the non-dominant hand) or blunt instrument is glided along the insertion vector to the medial canthus (e.g., from the insertion point (e.g., mark 1200, 1300) to the X (e.g., marking 1310) with a firm pressure. This step further suspends upward the deep fat pads and enhances the cheek curve.

In step 1710, the exposed thread is cut. The exposed thread can be cut by pushing down at the insertion site (e.g., mark 1200, 1300) with a firm pressure. Once the thread is cut and buried under the skin, the dimpling will subside. Gentle pressure may need to be applied at or around the insertion site to smooth out the dimple.

In step 1711, it is determined whether there are any additional cheek insertion points (e.g., pilot holes) that have not been used on the first anatomical side of the patient. If so (i.e., step 1711=yes), the method 1700 returns to step 1703 (via placeholder B) to insert the cannula into the next cheek insertion point on the first anatomical side of the patient, which proceeds as described above with a different or respective multidirectional barbed PDO thread. When there are no additional cheek insertion points on the first anatomical side of the patient (i.e., step 1711=no), the method 1700 proceeds to step 1712.

In step 1712, a cannula is inserted into the pilot hole proximal to the gonial angle (i.e., the pilot hole at marking 1410) on the first anatomical side of the patient. The cannula used in step 1712 can be the same as or different than the cannula used in steps 1703-1707. The cannula (e.g., L-shaped cannula 1800) contains a 100 mm a barbed PDO thread, such as a multi-directional laser cut PDO thread or a bi-directional molded PDO thread. The cannula is preferably 19 gauge but can be 18 gauge if the patient has thicker or heavier skin.

The cannula is inserted into the gonial angle pilot hole at a 90-degree angle with the cannula bevel up. After inserting the cannula, twist the cannula until the distal tip passes the dermis, approximately 2-3 mm. Unlike the cheek threads, the gonial angle threads are inserted and placed in the subcutaneous plane.

In step 1713, the angle of the cannula is lowered to about 0 degrees, substantially parallel to the skin surface.

In step 1714 (via placeholder C), the cannula is advanced along the gonial angle vector (e.g., along line 1501 or 1502). The most lateral gonial angle vector (i.e., line 1501) is preferably performed first. The cannula can be advanced using the non-dominant hand to pull the skin inferiorly, gently rotating the skin back and forth and advancing upward along the vector. The cannula outline should be clearly seen and felt under the skin. The cannula is advanced slowly and carefully, as it will be traversing vessels. If resistance is encountered, we gently redirect the cannula and rotate back and forth. The entire 100 mm length of the thread may be used for these gonial angle vectors in some examples. In an aspect, the cannula is advanced to the end point proximal to the hairline.

In step 1715, the cannula is removed. As the cannula is removed, we preferably press the skin with a non-dominant hand in an upward trajectory along the vector and twist/rotate the cannula 360 degrees, preferably more than a full rotation (e.g., 3-5 times) on exit. The exposed thread can then be cut in step 1716. We again remind the reader that the present examples are not limiting as to the quantitative parameters given, and are provided merely as examples of preferred embodiments, which those skilled in the art can modify to their required instances.

In step 1717, it is determined whether there are any additional gonial angle insertion points (e.g., pilot holes) on the first anatomical side of the patient that have not been used. If so (i.e., step 1717=yes), the method 1700 returns to step 1712 (via placeholder D) to insert the cannula into the next gonial angle insertion point, which proceeds as described above. When there are no additional gonial angle insertion points (i.e., step 1717=no), the method 1700 ends at step 1718.

In another embodiment, the gonial angle insertion vectors are performed before the cheek insertion vectors.

In step 1718, the procedures in steps 1703-1717 are repeated for the second anatomical side (e.g., anatomical right side 904) of the patient.

As can be seen, the present procedure is different from traditional methods of PDO thread lifting. The invention employs an inferior-to-superior insertion approach, as opposed to the traditional superior-to-inferior insertion approach in conventional thread lifting procedures. Thus, the insertion direction in the present procedure is opposite to the insertion direction in conventional thread lifting procedures. Also novel and non-obvious is the placement of the threads, which targets the deep fat pads as opposed to the superficial fat layer in placement of the threads in conventional thread lifting procedures. Thread placement and tissue plane were confirmed with a cadaver dissection employing the present technique. There are currently no documented thread lifting techniques inserting into the deep facial fat pads.

This present procedure works in multiple ways. In addition to repositioning the fat pads and slimming and contouring the face, the position of the present threads mimic the action of several facial ligaments, providing support and structure for the face. The present technique not only enhances the mid-facial curve, but also improves infraorbital hollowing and slims the lower face while creating a submalar contour, which is often a desirable aesthetic.

The PDO resorbable sutures used for facial suspension temporarily fixate the cheeks and mid face in an elevated position in patients with mild to moderate facial soft tissue ptosis and/or lower face fullness. The method of insertion as well as its aesthetic effect is vastly different from traditional PDO thread lifting.

A computer and computerized method may be provided in some aspects for automated planning, execution and display of the present invention. That is, a computer, program or application thereof may be used to assist an operator in planning the present processes, and/or these automated devices can be used to execute or help a human operator execute the present processes, as well as to illustrate, simulate or show (e.g., a subject or patient) any past, present or expected future scenario involving the procedure.

Figure 26:
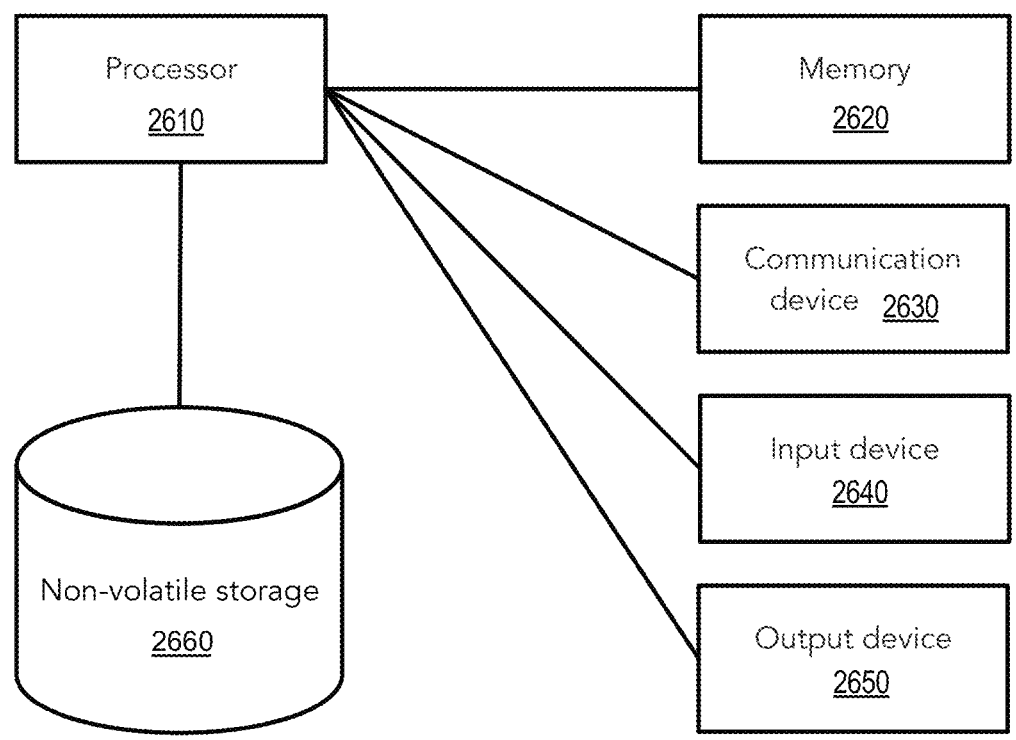
FIG. 26 is a block diagram of a computer system according to some embodiments.

FIG. 26 is a block diagram of a computer system 2600 according to some embodiments. The computer system 2600 includes one or more processors 2610, computer memory 2620, one or more communications devices 2630, an input device 2640, and an output device 2650. The computer system 2600 can also be coupled to one or more articles of manufacture that comprise non-transitory, non-volatile storage computer-readable storage media 2660.

The processor(s) 2610 include hardware microprocessors, central processing units, graphics processing units, and/or other processors. The processor(s) 2610 are operatively coupled to the computer memory 2620, communications device(s) 2630, input device 2640, and output device 2650. The computer memory 2620 and/or the non-transitory, non-volatile storage computer-readable storage media 2660 include computer-readable instructions that are executable the processor(s) 2610 to perform one or more tasks as described herein.

The communications device(s) 2630 can include a modem, a communication port, and/or a radio that can interconnect the computer system 2600 to one or more other devices and/or systems, such as, for example, one or more networks. The networks can include a local area network, a wide area network, a virtual private network, and/or another network. The network(s) can include a cellular network, a WiFi network, a short-range network (e.g., Bluetooth), and/or another type of network. The communication device(s) 2630 can be optional in some embodiments.

The input device 2640 can include a mouse, a touchpad, a touchscreen, a keyboard, a microphone (e.g., for speech recognition), a camera, and/or another input device. The output device 2650 can include a display screen (e.g., a computer monitor, a television, etc.), a printer, speakers, and/or another output device.

The computer-readable instructions can cause the processor(s) 2610 to generate an output on a display screen (e.g., on output device 2650) that includes graphical, textual, video, and/or audio instructions (e.g., step-by-step instructions) for performing any of the methods described herein (e.g., method 80 and/or method 1700). For example, the computer-readable instructions can cause the processor(s) 2610 to generate an output on the display screen that provides step-by-step instructions for marking a face to perform the present thread lifting technique (e.g., according to method 80). Additionally or alternatively, the computer-readable instructions can cause the processor(s) 2610 to generate an output on the display screen that provides step-by-step instructions for performing the present thread lifting technique (e.g., according to method 1700).

In some embodiments, a camera (e.g., input device 2640) can capture images of the surgeon marking a patient face (e.g., according to method 80) and the computer-readable instructions can cause the processor(s) 2610 to compare the images with pre-stored images of an example surgeon correctly marking an example face to determine whether the surgeon is marking the patient face correctly. The computer-readable instructions can include artificial intelligence, such as a trained neural network, that causes the processor(s) 2610 to predict whether the surgeon is marking the patient face correctly. The computer-readable instructions can cause the processor(s) 2610 to generate an output signal when the artificial intelligence predicts that the surgeon is marking the patient face incorrectly. The output signal can include an audible signal (e.g., a warning sound), a visual signal (e.g., a light), and/or corrective instructions for the surgeon to correct one or more marking errors.

Additionally or alternatively, the camera (e.g., input device 2640) can capture images of the surgeon performing the present thread lifting technique (e.g., according to method 1700) and the computer-readable instructions can cause the processor(s) 2610 to compare the images with pre-stored images of an example surgeon correctly performing the present thread lifting technique to determine whether the surgeon is performing the Cheek Pop thread lifting technique correctly. The computer-readable instructions can include artificial intelligence, such as a trained neural network, that causes the processor(s) 2610 to predict whether the surgeon is performing the present thread lifting technique correctly. The computer-readable instructions can cause the processor(s) 2610 to generate an output signal when the artificial intelligence predicts that the surgeon is performing the present thread lifting technique incorrectly. The output signal can include an audible signal (e.g., a warning sound), a visual signal (e.g., a light), and/or corrective instructions for the surgeon to correct one or more surgical errors.

The invention should not be considered limited to the particular embodiments described above. Various modifications, equivalent processes, as well as numerous structures to which the invention may be applicable, will be readily apparent to those skilled in the art to which the invention is directed upon review of this disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in field programmable gate arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of this application need not reside on a single computer or processor, but may be distributed in a modular fashion among a number of different computers or processors to implement various aspects of this application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the disclosure and claims include new and novel improvements to existing methods and technologies, which were not previously known nor implemented to achieve the useful results described above. Users of the method and system will reap tangible benefits from the functions now made possible on account of the specific modifications described herein causing the effects in the system and its outputs to its users. It is expected that significantly improved processes can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A method comprising:
    (a) forming pilot holes at respective insertion points on a first anatomical side of a patient, the respective insertion points comprising:
        a first cheek insertion point located about 1.5 cm along a submalar contour line of the patient from a nasolabial fold line of the patient;
        a plurality of additional cheek insertion points spaced about 1 cm from each other along the submalar contour line, the additional cheek insertion points including a second cheek insertion point located about 1 cm along the submalar contour line from the first cheek insertion point; and
        a gonial angle insertion point located about 2 cm superior to a gonial angle of the patient;
    (b) inserting a first cannula into a first pilot hole at the first cheek insertion point, the first cannula having an L-shaped distal end, the first cannula containing a first multidirectional barbed polydioxanone (PDO) thread, the first cannula oriented at an angle of about 90 degrees with respect to a skin surface of the patient;
    (c) advancing the first cannula about 3 mm to about 5 mm into the first pilot hole while maintaining the angle of the first cannula at about 90 degrees with respect to the skin surface of the patient;
    (d) reducing the angle of the first cannula to about 10 degrees with respect to the skin surface of the patient;
    (e) advancing the first cannula about 1 cm while maintaining the angle of the first cannula at about 10 degrees with respect to the skin surface of the patient so as to advance the first cannula into one or more deep cheek fat pads;
    (f) reducing the angle of the first cannula to about 0 degrees with respect to the skin surface of the patient;
    (g) advancing, while maintaining the angle of the first cannula at about 0 degrees with respect to the skin surface of the patient, the first cannula along a cheek insertion vector to an end point that represents a levator labii superioris alaeque nasi of the patient, whereby the cheek insertion vector extends in an inferior-to-superior direction through the one or more deep cheek fat pads;
    (h) removing the first cannula from the first cheek insertion point;
    (i) cutting an exposed portion of the first multidirectional barbed PDO thread;
    (j) repeating steps (b) through (h) for each of the additional cheek insertion points using a respective multidirectional barbed PDO thread;
    (k) inserting a second cannula into a gonial angle pilot hole at the gonial angle insertion point, the second cannula containing a second PDO thread, the second cannula oriented at an angle of about 90 degrees with respect to the skin surface of the patient;
    (l) advancing the second cannula about 2 mm to about 3 mm into the gonial angle pilot hole while maintaining the angle of the second cannula at about 90 degrees with respect to the skin surface of the patient;
    (m) reducing the angle of the second cannula to about 0 degrees with respect to the skin surface of the patient;
    (n) advancing the second cannula along a first gonial angle vector while maintaining the angle of the second cannula at about 0 degrees with respect to the skin surface of the patient, the first gonial angle vector beginning at the gonial angle insertion point and ending at a hairline of the patient along a first line, the first line passing about 1 cm from a tragus of the patient, whereby the first gonial angle vector extends in an inferior-to-superior insertion direction;
    (o) removing the second cannula from the gonial angle insertion point;
    (p) cutting an exposed portion of the second PDO thread;
    (q) inserting the second cannula into the gonial angle pilot hole at the gonial angle insertion point, the second cannula containing a third PDO thread, the second cannula oriented at the angle of about 90 degrees with respect to the skin surface of the patient;
    (r) advancing the second cannula about 2 mm to about 3 mm into the gonial angle pilot hole while maintaining the angle of the second cannula at about 90 degrees with respect to the skin surface of the patient;
    (s) reducing the angle of the second cannula to about 0 degrees with respect to the skin surface of the patient;
    (t) advancing the second cannula along a second gonial angle vector while maintaining the angle of the second cannula at about 0 degrees with respect to the skin surface of the patient, the second gonial angle vector beginning at the gonial angle insertion point and ending at a hairline of the patient along a second line that is medial to the first line, the second line passing about 3 cm lateral to a lateral canthus of the patient along a horizontal line that passes through the lateral canthus, the second gonial angle vector extends in the inferior-to-superior insertion direction;
    (u) removing the second cannula from the gonial angle insertion point; and
    (v) cutting an exposed portion of the third PDO thread.

2. The method of claim 1, wherein the first cannula is different than the second cannula.

3. The method of claim 1, wherein after removing the first cannula from the first cheek insertion point, a dimple in the patient is located at the first cheek insertion point and the method further comprises (w) pushing the dimple of the patient inwardly along the first multidirectional barbed PDO thread.

4. The method of claim 3, further comprising (x) pressing a finger along the cheek insertion vector to suspend upwards one or more deep fat pads in the patient.

5. The method of claim 4, wherein step (j) comprises repeating steps (b) through (h), (w), and (x) for each of the additional cheek insertion points, the first cannula being advanced along a respective cheek insertion vector at each additional cheek insertion point.

6. The method of claim 1, further comprising rotating the first cannula while removing the first cannula from the first cheek insertion point.

7. The method of claim 1, further comprising rotating the second cannula while removing the second cannula from the gonial angle insertion point in steps (o) and (u).

8. The method of claim 1, further comprising repeating steps (a) through (v) on a second anatomical side of the patient.

9. The method of claim 8, wherein the first anatomic side of the patient is an anatomical left side of the patient and the second anatomic side of the patient is an anatomical right side of the patient.

10. The method of claim 1, wherein:
the second PDO thread comprises a second multidirectional barbed PDO thread or a second bi-directional barbed PDO thread, and
the third PDO thread comprises a third multidirectional barbed PDO thread or a third bi-directional barbed PDO thread.

11. A computer-implemented method for displaying graphical instructions for performing a surgical procedure, the method comprising displaying, on a display screen in electrical communication with the computer, a graphical illustration of each step of the method of claim 1.

12. A method of marking a face of a patient for a surgical procedure, the method comprising:
on a first anatomical side of the patient:
(a) marking on the patient, with a surgical marking pen, a first line on a nasolabial fold line of the patient;
(b) drawing on the patient, with the surgical marking pen, a horizontal line starting at a lateral canthus of the patient, the horizontal extending at least 2 cm in length;
(c) drawing on the patient, with the surgical marking pen, a vertical line from the horizontal line to a mandible of the patient, the vertical line intersecting the horizontal line at a point about 2 cm from a respective lateral canthus of the patient, the vertical line orthogonal to the horizontal line;
(d) drawing on the patient, with the surgical marking pen, a submalar contour line from an oral commissure of the patient to a lower tragus of the patient;
(e) marking on the patient, with the surgical marking pen, a first cheek insertion point on the submalar contour line, the first cheek insertion point located about 1.5 cm lateral to the first line;
(f) marking on the patient, with the surgical marking pen, additional cheek insertion points on the submalar contour line, the additional cheek insertion points spaced about 1 cm from each other along the submalar contour line, the additional cheek insertion points including a second cheek insertion point located about 1 cm along the submalar contour line from the first cheek insertion point;
(g) marking on the patient, with the surgical marking pen, a levator labii superioris alaeque nasi of the patient;
(h) marking on the patient, with the surgical marking pen, a gonial angle of the patient;
(i) marking on the patient, with the surgical marking pen, a gonial angle insertion point on the patient, the gonial angle insertion point located about 2 cm above the gonial angle and anterior to an earlobe of the patient;
(j) drawing on the patient, with the surgical marking pen, a first line on the patient, the first line extending from the gonial angle insertion point to a hairline of the patient, the first line passing about 1 cm from a tragus of the patient, the first line representing a first gonial angle vector that extends in an inferior-to-superior insertion direction from the gonial angle insertion point to the hairline; and
(k) drawing, with the surgical marking pen, a second line on the patient, the second line extending from the gonial angle insertion point to the hairline, the second line medial to the first line and passing about 1 cm from the point of intersection of the horizontal and vertical lines, the second line representing a second gonial angle vector that extends in an inferior-to-superior insertion direction from the gonial angle insertion point to the hairline.

13. The method of claim 12, further comprising drawing a plurality of cheek lines on the patient, the cheek lines including:
a first cheek line that extends from the first cheek insertion point to a mark on the levator labii superioris alaeque nasi,
a second cheek line that extends from the second cheek insertion point to the mark on the levator labii superioris alaeque nasi, and
a plurality of additional cheek lines, each additional cheek line extends from a respective additional cheek insertion point to the mark on the levator labii superioris alaeque nasi,
wherein the plurality of cheek lines represent respective cheek vectors that extend in the inferior-to-superior insertion direction.

14. The method of claim 12, further comprising repeating steps (a) through (k) on a second anatomical side of the patient.

15. The surgical method of claim 14, wherein the first anatomic side of the patient is an anatomical left side of the patient and the second anatomic side of the patient is an anatomical right side of the patient.

16. A computer-implemented method for displaying graphical instructions for marking a face of a patient for a surgical procedure, the method comprising displaying, on a display screen in electrical communication with the computer, a graphical illustration of each step of the method of claim 12.

* * * * *